United States Patent [19]

Sendai et al.

[11] Patent Number: 5,459,260
[45] Date of Patent: Oct. 17, 1995

[54] TRICYCLIC OR TETRACYCLIC CARBAPENEM COMPOUNDS, THEIR PRODUCTION AND USE

[75] Inventors: Michiyuki Sendai, Osaka; Tetsuo Miwa, Hyogo, both of Japan

[73] Assignee: Takeda Chemical Industries, Ltd., Osaka, Japan

[21] Appl. No.: 124,999

[22] Filed: Sep. 22, 1993

Related U.S. Application Data

[63] Continuation of Ser. No. 863,980, Apr. 6, 1992, abandoned.

[30] Foreign Application Priority Data

Apr. 5, 1991 [JP] Japan .................................. 3-072979

[51] Int. Cl.$^6$ .................... C07D 487/14; C07D 471/14; C07D 491/14; C07D 495/14; C07D 497/14; A61K 31/40
[52] U.S. Cl. .................................................. 540/302
[58] Field of Search ............................ 540/302; 514/210

[56] References Cited

U.S. PATENT DOCUMENTS

| | | | |
|---|---|---|---|
| 4,036,969 | 7/1977 | Stirling | 540/302 X |
| 4,374,848 | 2/1983 | Christensen et al. | 540/302 X |
| 4,374,849 | 2/1983 | Christensen et al. | 540/302 X |
| 4,600,713 | 7/1986 | Christensen et al. | 540/302 X |
| 5,021,565 | 6/1991 | Ratcliffe et al. | 540/302 |

FOREIGN PATENT DOCUMENTS

| | | | |
|---|---|---|---|
| 0292191 | 11/1988 | European Pat. Off. | 540/302 |
| 416953 | 3/1991 | European Pat. Off. | 540/302 |
| 0422596 | 4/1991 | European Pat. Off. | 540/302 |
| 2183237 | 6/1987 | United Kingdom | 540/302 |

OTHER PUBLICATIONS

Tetrahedron Letters, vol. 25, No. 26, 1984, pp. 2793–2796. Yoshida et al.
Tetrahedron Letters, vol. 22, No. 50, 1981, pp. 5027–5030, Heck et al.

*Primary Examiner*—Floyd D. Higel
*Attorney, Agent, or Firm*—Foley & Lardner

[57] ABSTRACT

A polycyclic carbapenem compound of the formula (Ia'), (Ib') or (Ic')

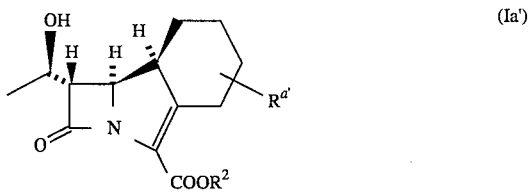

(Ia')

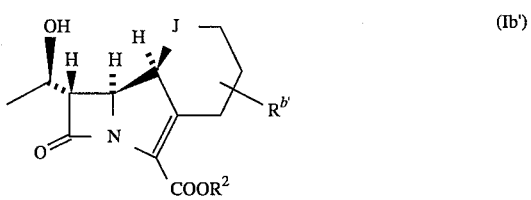

(Ib')

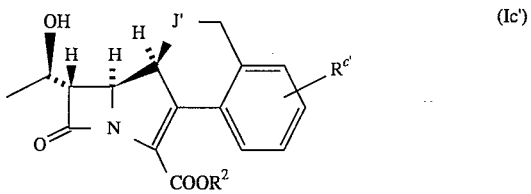

(Ic')

[wherein COOR$^2$ is a carboxy group which may be esterified; R$^{a'}$ is —(CH$_2$)$_m$—K$^a$—(CH$_2$)$_n$—U$^{a'}$; J is O or S; R$^{b'}$ is —(CH$_2$)$_m$—K$^b$—(CH$_2$)$_n$U$^{b'}$; J' is O, S or CH$_2$; R$^{c'}$ is —(CH$_2$)$_m$—K$^c$—(CH$_2$)$_n$—U$^{c'}$, —(CH$_2$)$_m$—K$^d$—(CH$_2$)$_n$—U$^d$ or a pair of groups, one of which is a hydroxy group, with the other being a hydroxzy group or an alkylsulfonylamino group, which may be substituted, in the position ortho to the first-mentioned hydroxy group] or a salt thereof are useful as an antibacterial agent.

11 Claims, No Drawings

TRICYCLIC OR TETRACYCLIC CARBAPENEM COMPOUNDS, THEIR PRODUCTION AND USE

This application is a continuation of U.S. application Ser. No. 07/863,980 filed Apr. 6, 1992, now abandoned.

The present invention relates to novel polycyclic carbapenem compounds and their salts. The polycyclic carbapenem compounds and salts of the invention are used as an antibacterial agent.

A number of reports are available on carbapenem antibiotics represented by thienamycin (e.g. Robert B. Morin, Marvin Gorman: Chemistry and Biology of β-Lactam Antibiotics, vol. 2, p. 227, Academic Press Inc., 1982). As to polycyclic carbapenem compounds, a compound having the chemical formula shown below is described in Tetrahedron Letters 22, 5027 (1981).

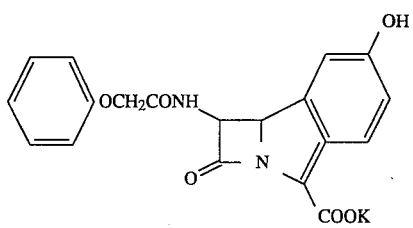

However, the compounds of the present invention are novel compounds structurally distinguished from the hitherto-known compounds referred to above.

Carbapenem compounds generally have excellent antibacterial activity but are not satisfactory in chemical stability and in resistance to renal dehydropeptidase-I (DHP-I). For this reason, there has been a pressing need for the advent of carbapenem compounds not only having sufficiently high antibacterial activity but also satisfactory in in vivo stability and good pharmacokinetics.

The object of the present invention is to provide such carbapenem compounds.

In their endeavor to accomplish the above object, the inventors of the present invention explored various carbapenem compounds and have succeeded in creating compounds having entirely new structures represented below by formulas (Ia), (Ib) and (Ic). They found that these compounds have excellent antibacterial activity and perfected the present invention.

Thus, the present invention is directed to a tricyclic carbapenem compound of the formula (Ia):

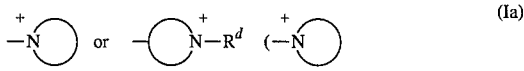

(Ia)

[wherein $R^1$ is a hydrogen atom or an optionally substituted lower alkyl, lower alkenyl, lower alkynyl or cycloalkyl group; $COOR^2$ is a carboxy group which may be esterified; ring A is a cyclohexane or cyclohexene ring; $R^a$ is a group of the formula $-W^a-U^a$ {$W^a$ is a bond, sulfur (which may be in the form of mono- or dioxide), oxygen, NH (which may be substituted) or a straight-chain or branched lower alkylene or alkenylene group which may be interrupted by sulfur (which may be in the form of mono- or dioxide), oxygen or NH (which may be substituted); $U^a$ is carbamoyl, acyl which may be substituted, alkylammonium which may be substituted or a group of the formula

is a quaternized nitrogen-containing heterocyclic group which may be substituted and $R^d$ is an alkyl group which may be substituted)}, $R^a$ may occur in units of 1 to 3] or a salt thereof;

a tricyclic carbapenem compound of the formula (Ib):

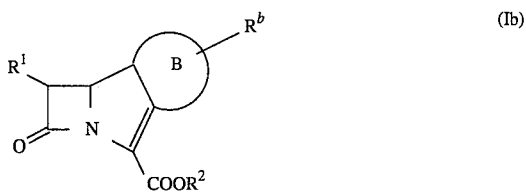

(Ib)

[wherein $R^1$ and $COOR^2$ are as defined hereinabove; ring B is a saturated or unsaturated six-membered heterocycle; is $R^b$ is 1) an alkyloxycarbonyl group or 2) a group of the formula $-W^b-U^b$ {$W^b$ is a bond, sulfur (which may be in the form of mono- or dioxide), oxygen, NH (which may be substituted) or a straight-chain or branched lower alkylene or lower alkenylene group which may be interrupted by sulfur (which may be in the form of mono- or dioxide), oxygen or NH (which may be substituted); $U^b$ is a) an optionally substituted aromatic hydrocarbon or heterocyclic group, b) a cyano, amino, carbamoyl, carboxy, sulfamoyl, halogen, amidino, hydroxy or methyl group, c) an optionally substituted alkylamino, alkylammonium, acylamino, alkyloxy, alkylthio, alkylsulfonyl, alkylsulfonylamino, acyloxy or alkylcarbamoyl group or d) a group of the formula

is a quaternized nitrogen-containing heterocyclic group which may be substituted; $R^d$ is an alkyl group which may be substituted)}, $R^b$ may occur in units of 1 to 3] or a salt thereof;

a tetracyclic carbapenem compound of the formula (Ic):

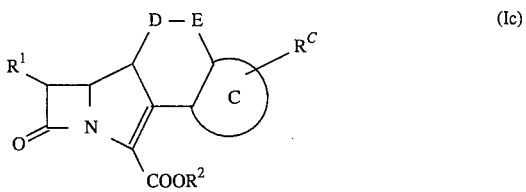

(Ic)

[wherein $R^1$ and $COOR^2$ are as defined hereinabove; D and E each is $CH_2$, O, S or NH; ring C is a benserie ring or a 5- or 6-membered aromatic heterocycle; $R^c$ is 1) an optionally substituted alkylammoniumalkyloxy, alkylaminoalkyloxy or alkylsulfonylaminoalkyloxy group, 2) a group of the formula $-W^c-U^c$ {$W^c$ is a bond, a sulfur (which may be in the form of mono- or dioxide) or NH (which may be substituted) or a straight-chain or branched lower alkylene or lower alkenylene group which may be interrupted by sulfur (which may be in the form of mono- or dioxide) of NH (which may be substituted); $U^c$ is a) an optionally substituted aromatic hydrocarbon or heterocyclic group b) a cyano, amino, carbamoyl, carboxy, sulfamoyl, halogen, amidino, hydroxy or methyl group, c) an optionally substituted alkylamino, alkylammonium, acylamino, alkyloxy, alkylthio, alkylsulfonyl, alkylsulfonylamino, acyloxy or alkylcarbamoyl group or d) a group of the formula

is a quaternized nitrogen-containing heterocyclic group which may be substituted; $R^d$ is an alkyl group which may be substituted)} or 3) a group of the formula

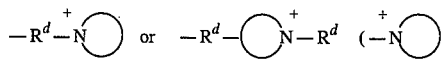

and $R^d$ are as defined above; $W^d$ is an oxygen atom or a straight-chain or branched lower alkylene or alkenylene group which may be interrupted by oxygen), $R^c$ may occur in units of 1 to 3] or a salt thereof.

The present invention also relates to processes for producing said compounds and salts, and antibacterial compositions comprising any of said compounds and salts.

Regarding the above units, it is to be understood that each of the rings A, B and C may be substituted by one to three substituents of $R^a$, $R^b$ and $R^c$.

Compounds (Ia), (Ib) and (Ic), as well as salts thereof, which are provided by the present invention, exhibit excellent antibacterial activity against a broad spectrum of pathogenic microorganisms including gram-positive and gram-negative bacteria.

Referring to the above formulas (Ia), (Ib) and (Ic), $R^1$ is a hydrogen atom or an optionally substituted lower alkyl, lower alkenyl, lower alkynyl or cycloalkyl group. The lower alkyl group is a straight-chain or branched alkyl group having 1 to 6 carbon atoms, such as methyl, ethyl, n-propyl, isopropyl, n-butyl, isobutyl, sec-butyl, tert-butyl, n-pentyl, n-hexyl and so on. The lower alkenyl group is a straight-chain or branched alkenyl group having 3 to 6 carbon atoms, such as propenyl, butenyl, pentenyl and so on. The lower alkynyl group is an alkynyl group having 3 to 6 carbon atoms, such as propynyl, butynyl, pentynyl and so on. The cycloalkyl groups is a cycloalkyl group of 3 to 6 carbon atoms, such as cyclopropyl, cyclobutyl, cyclopentyl, cyclohexyl and so on. These lower alkyl, lower alkenyl, lower alkynyl and cycloalkyl groups may be substituted by 1 to 3 substituent groups, which may be the same or different, such as cyano, amino, mono- or di-($C_1$–$C_4$)alkylamino (e.g. methylamino, ethylamino, propylamino, isopropylamino, butylamino), hydroxy, ($C_1$–$C_4$)alkyloxy, carbamoyloxy, ($C_1$–$C_4$)alkylthio, ($C_1$–$C_4$)alkylsulfonyl, halogen (e.g. fluorine, chlorine, bromine), sulfamoyl, ($C_1$–$C_4$)alkoxycarbonyl (e.g. methoxycarbonyl, ethoxycarbonyl, propoxycarbonyl, butoxycarbonyl) and sulfoxy. $R^1$ is preferably a hydroxyalkyl group, more desirably a 1-hydroxyethyl group and still more desirably (1R)-hydroxyethyl.

In the above formulas (Ia), (Ib) and (Ic), the ester residue $R^2$ of esterified carboxy $COOR^2$ may be any of the ester residues which are commonly employed in the field of β-lactam compounds such as cephalosporins forming easily-cleavable groups, for example which form easily biologically hydrolized esters at the 4-position of cephalosporin compounds, (esters which can provide the so-called prodrugs) or those groups which are commonly used as carboxylic acid ester residues in the field of medicinal science.

To be more specific, groups of the formula

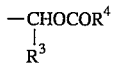

[wherein $R^3$ is a hydrogen atom or an alkyl, cycloalkyl or cycloalkylalkyl group; $R^4$ is a hydrogen atom or an alkyl, cycloalkyl, alkoxy, cycloalkyloxy, cycloalkylalkyl, alkenyloxy or phenyl group), phthalidyl, (2-oxo-5-methyl-1,3-dioxol-4-yl)methyl, alkoxyalkyl, alkylthioalkyl, tert-butyl, 2,2,2-trichloroethyl, benzyl, p-methoxybenzyl, p-nitrobenzyl, o-nitrobenzyl, phenethyl, bis(methoxyphenyl)methyl, 3,4-dimethoxybenzyl, benzhydryl, trityl, trimethylsilyl, 2-trimethylsilylethyl, allyl, etc.] can be employed.

Referring to the above formulas, the alkyl group represented by $R^3$ or $R^4$ or the alkyl moiety of the alkoxyalkyl or alkylthioalkyl group in the above ester residue may be a straight-chain or branched alkyl group of, for example, 1 to 6 carbon atoms (e.g. methyl, ethyl, propyl, isopropyl, butyl, 2,2-dimethylpropyl, etc.). By the same token, the cycloalkyl group or the cycloalkyl moiety of the cycloalkyloxy or cycloalkylalkyl group may be a cycloalkyl group of, for example, 3 to 7 carbon atoms (e.g. cyclopropyl, cyclobutyl, cyclopentyl, cyclohexyl, cycloheptyl, etc.). The alkoxy group $R^4$ or the alkoxy moiety of the alkoxyalkyl group in said ester residue may be a straight-chain or branched alkoxy group of, for example, 1 to 10 carbon atoms (e.g. methoxy, ethoxy, propoxy, isopropoxy, butoxy, hexyloxy, decyloxy, etc.). The alkenyloxy group $R^4$ may be a straight-chain or branched alkenyloxy group of, for example, 2 to 7 carbon atoms (e.g. allyloxy, etc.)

As particularly preferred examples of ester residue $R^2$, there may be mentioned those groups which are suitable for oral administration and give biologically labile ester derivatives, such as acetoxymethyl, 1-acetoxyethyl, 1-acetoxypropyl, pivaloyloxymethyl, 1-isopropyloxycarbonyloxyethyl, 1-cyclohexyloxycarbonyloxyethyl, phthalidyl, (2-oxo-5-methyl-1,3-dioxol-4-yl)methyl and so on.

The substituted cyclic group represented by ring A or B is a cyclic group which is formed in association with the carbon atoms in positions 1 and 2 of a carbapenem compound of the formula

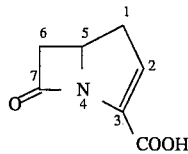

Ring A is a cyclohexane or cyclohexene group and preferably cyclohexane.

The saturated or unsaturated six-membered heterocyclic group as ring B is preferably a heterocycle containing 1 to 2 hetero-atoms selected from among N, S (which may be in the form of mono- or dioxide), O, etc. and not more than one unsaturated bond. Examples of such heterocycle include tetrahydropyran, dihydropyran, tetrahydrothiopyran, dihydrothiopyran, dioxane, dithiane, oxathiane, piperidine, piperazine, hexahydropyridazine, morpholine and so on.

Ring B is preferably a saturated six-membered heterocycle containing 1 to 2 hetero-atoms such as sulfur and oxygen atoms such as tetrahydropyran, tetrahydrothiopyran, dioxane, dithiane and so on.

Ring C is a benzene ring or a 5- or 6-membered aromatic heterocycle. The 5- or 6-membered aromatic heterocycle as ring C is a heterocycle containing 1 to 3 hetero-atoms such as nitrogen, oxygen and sulfur atoms, such as furan, thiophene, thiazole, isothiazole, oxazole, isoxazole, pyrazole, imidazole, thiadiazole, triazole, pyridine, pyrimidine, pyridazine, pyran and so on. Preferably, ring C is a benzene ring.

D and E each is $CH_2$, S, O or NH and a preferred combination is D being $CH_2$, O or S and E being $CH_2$.

The number of the substituent group $R^a$ on ring A may be 1 to 3, which may be the same or different. $R^a$ is a group of the formula $-W^a-U^a$ {$W^a$ is a bond, a sulfur (which may be in the form of mono- or dioxide), oxygen or NH (which may be substituted) or a straight-chain or branched lower alkylene or lower alkenylene group which may be interrupted by sulfur (which may be in the form of mono- or dioxide), oxygen or NH (which may be substituted); $U^a$ is a carbamoyl, acyl which may be substituted, alkylammonium which may be substituted or a group of the formula

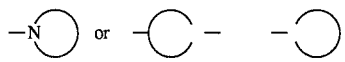

is a quaternized nitrogen-containing heterocyclic group which may be substituted; $R^d$ is an alkyl group which may be substituted)}.

The number of the substituent group $R^b$ on ring B may be 1 to 3, which may be the same or different, and is selected from the groups mentioned below as 1) or 2). Thus, $R^b$ is 1) an alkyloxycarbonyl group or 2) a group of the formula $-W^b-U^b$ {$W^b$ is a bond, a sulfur (which may be in the form of mono- or dioxide), oxygen, NH (which may be substituted), or a straight-chain or branched lower alkylene or lower alkenylene group which may be interrupted by sulfur (which may be in the form of mono- or dioxide), oxygen or NH (which may be substituted); $U^b$ is a) an optionally substituted aromatic hydrocarbon or heterocyclic group, b) a cyano, amino, carbamoyl, carboxy, sulfamoyl, halogen, amidino, hydroxy or methyl group, c) an optionally substituted alkylamino, alkylammonium, acylamino, alkyloxy, alkylthio, alkylsulfonyl, alkylsulfonylamino, acyloxy or alkylcarbamoyl group, or d) a group of the formula

is a quaternized nitrogen-containing heterocyclic group which may be substituted; $R^d$ is an alkyl group which may be substituted)}.

The number of the substituent group $R^c$ on ring C may be 1 to 3, which may be the same or different, and can be selected from among the substituent groups mentioned below as 1) to 3). Thus, $R^c$ is 1) an optionally substituted alkylammoniumalkyloxy, alkylaminoalkyloxy or alkylsulfonylaminoalkyloxy group, 2) a group of the formula $-W^c-U^c$ {$W^c$ is a bond, a sulfur (which may be in the form of mono- or dioxide) or NH (which may be substituted) or a straight-chain or branched lower alkylene or lower alkenylene group which may be interrupted by sulfur (which may be in the form of mono- or dioxide) or NH (which may be substituted); $U^c$ is a) an optionally substituted aromatic hydrocarbon or heterocyclic group, b) a cyano, amino, carbamoyl, carboxy, sulfamoyl, halogen, amidino, hydroxy or methyl group, c) an optionally substituted alkylamino, alkylammonium, acylamino, alkyloxy, alkylthio, alkylsulfonyl, alkylsulfonylamino, acyloxy or alkylcarbamoyl group, or d) a group of the formula

is a quaternized nitrogen-containing heterocyclic group which may be substituted; $R^d$ is an alkyl group which may be substituted)} or 3) a group of the formula

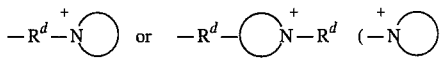

and $R^d$ are as defined hereinbefore; $W^d$ an oxygen atom or a straight-chain or branched lower alkylene or lower alkenylene group which may be interrupted by oxygen).

The substituent group or groups which can be employed for said an optionally substituted "NH", "aromatic hydrocarbon", "heterocyclic" "alkylamino", "alkylammonium", "acyl", "acylamino", "alkyloxy", "alkylsulfonyl", "alkylsulfonylamino", "acyloxy", "alkylcarbamoyl", "alkyloxycarbonyl", "alkylammoniumalkyloxy", "alkylaminoalkyloxy", "alkylsulfonylaminoalkyloxy", "quaternized nitrogen-containing heterocyclic" or "alkyl" group include, among others, $(C_1-C_6)$alkyl, $(C_2-C_6)$alkenyl (e.g. vinyl, butenyl, propenyl, etc.), $(C_6-C_{10})$aryl (e.g. phenyl and naphthyl), $(C_7-C_{12})$aralkyl (e.g. phenyl-$(C_1-C_6)$alkyl), $(C_3-C_6)$cycloalkyl (e.g. cyclopropyl, cyclobutyl, cyclopentyl, etc.), a 4- to 6-membered heterocyclic group containing 1 to 4 hetero-atoms such as nitrogen, oxygen and/or sulfur, cyano, amino, mono- or di$(C_1-C_4)$alkylamino, acylamino, hydroxy, $(C_1-C_4)$alkyloxy, acyloxy, carbamoyloxy, mono- or di$(C_1-C_4)$alkylcarbamoyloxy, $(C_1-C_4)$alkylthio, $(C_1-C_4)$alkylsulfinyl, $(C_1-C_4)$alkylsulfonyl, $(C_1-C_4)$ alkylsulfonylamino, halogen (e.g. fluorine, chlorine, bromine, etc.), sulfamoyl, mono- or di$(C_1-C_4)$alkylsulfamoyl, $(C_1-C_4)$alkoxycarbonyl, carboxy, carbamoyl, mono- or di$(C_1-C_4)$alkylcarbamoyl and so on. The aromatic hydrocarbon moiety of said "aromatic hydrocarbon group which may be substituted" is preferably benzene or naphthalene.

The alkyl moiety of said optionally substituted "alkylamino", "alkylammonium", "alkyloxy", "alkylsulfonyl", "alkylsulfonylamino", "alkylcarbamoyl", "alkyloxycarbonyl", "alkylammoniumalkyloxy", "alkylaminoalkyloxy", "alkylsulfonylaminoalkyloxy" or "alkyl" group is preferably a straight-chain or branched $C_1-C_6$ alkyl group.

As the heterocycle of said "heterocyclic group which may be substituted" or said 4- to 6-membered heterocyclic group containing 1 to 4 hetero-atoms, there can be employed azetidine, furan, pyrrole, pyrrolidine, thiophene, tetrahydrothiophene, thiazole, isothiazole, thiazoline, thiazolidine, oxazole, isoxazole, oxazoline, oxazolidine, pyrazole, pyrazoline, imidazole, imidazoline, thiadiazole, triazole, tetrazole, pyridine, pyrimidine, pyridazine, triazine, morpholine, piperazine, piperidine, quinuclidine and so on.

The acyl moiety of said optionally substituted "acyl", "acyloxy" or "acylamino" is preferably a $C_1-C_6$ alkanoyl (e.g. formyl, acetyl, propionyl, butyryl), a $C_1-C_6$ alkenoyl (e.g. acryloyl, crotonoyl), cycloalkanecarbonyl (e.g. cyclopropanecarbonyl, cyclobutanecarbonyl), aroyl (e.g. benzoyl, p-toluoyl), aryl-$C_1$-$C_6$ alkanoyl (e.g. phenylacetyl, phenylpropionyl), aromatic heterocyclic carbonyl (e.g. furoyl, thenoyl, nicotinoyl, isonicotinoyl), aromatic heterocyclic alkanoyl (e.g. thienylacetyl, thiazolylacetyl, pyridylacetyl), nonaromatic heterocyclic carbonyl (e.g. pyrrolidinylcarbonyl, piperidinylcarbonyl) and so on.

The quaternized nitrogen-containing heterocyclic group which may be substituted, as designated by the formula

is preferably a quaternized monocyclic or bicyclic nitrogen-containing heterocyclic group which may be substituted and a quaternized 5- or 6-membered monocyclic nitrogen-containing heterocyclic group containing 1 to 3 hetero-atoms or a quaternized 8- to 10-membered bicyclic nitrogen-containing heterocyclic group containing 1 to 5 hetero-atoms can be employed. Typical examples of said quaternized monocyclic or bicyclic nitrogen-containing heterocyclic group are pyridinium, pyridazinium, pyrimidinium, pyrazinium, pyrazolium, triazolium, imidazolium, thiazolium, oxazolium, thiadiazolium, isothiazolium, isoxazolium, N-methylpyrrolidinium, quinolinium, isoquinolinium, quinoxalinium, isocinnolinium, thienopyridinium, imidazolopyridinium, imidazolopyridazinium, triazolopyridinium, triazolopyridazinium, triazolopyridazinium, quinuclidinium, dihydropyrazolotriazolium and so on.

Formula (Ia) more preferably represents a tricyclic carbapenem compound of the formula (Ia'):

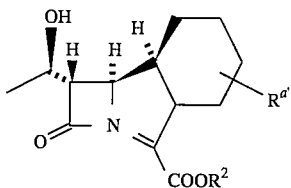

wherein $COOR^2$ is as defined hereinbefore; $R^{a'}$ is a group of the formula $—(CH_2)_m—K^a—(CH_2)_n—U^{a'}$ [where $K^a$ is $CH_2$, O, S or NH; m and n each is a whole number of 0 to 3; $U^{a'}$ is a group of the formula

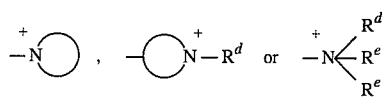

(wherein

and $R^d$ are as defined hereinbefore and $R^a$ is an alkyl group which may be substituted) or a salt thereof.

Formula (Ib) more preferably represents a tricyclic carbapenem compound of formula (Ib'):

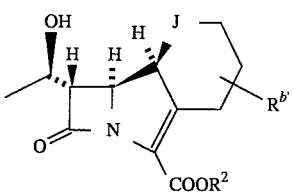

[wherein $COOR^2$ is as defined hereinbefore; J is O or S; $R^{b'}$ is a group of the formula $—(CH_2)_m—K^b—(CH_2)_n—U^{b'}$ {where is $K^b$ is $CH_2$, O, S or NH; m and n each is a whole number of 0 to 3; $U^{b'}$ is (1) a group of the formula

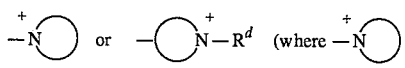

and $R^d$ are as defined hereinbefore), (2) a basic group such as amino, alkylamino, amidino, alkylamidino, etc. or a basic heterocyclic group (e.g. pyrrolidine) or (3) a group of the formula

where $R^d$ and $R^a$ each is an alkyl group which may be substituted)} or a salt thereof.

Formula (Ic) more preferably represents a tetracyclic carbapenem compound of the formula (Ic'):

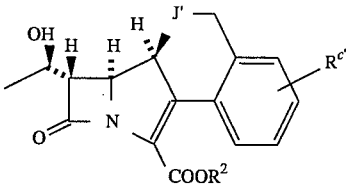

[wherein $COOR^2$ is as defined hereinbefore; J' is O, S or $CH_2$; $R^{c'}$ is

[1] a group of the formula $—(CH_2)_m—K^c—(CH_2)_n—U^{c'}$ {where $K^c$ is $CH_2$, S or NH; m and n each is a whole number of 0 to 3; $U^{c'}$ is (1) a group of the formula

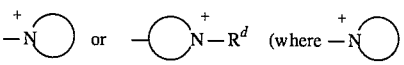

and $R^d$ are as defined hereinbefore), (2) a basic group such as amino, alkylamino, amidino, alkylamidino, etc. or a basic heterocyclic group (e.g. pyrrolidine) or (3) a group of the formula

(where $R^d$ and $R^a$ each is an alkyl group which may be substituted)] or [2] a group of the formula $—(CH_2)_m—K^d—(CH_2)_n—U^d$ (where $K^d$ is O; m and n each is a whole number of 0 to 3; $U^d$ is (1) a group of the formula

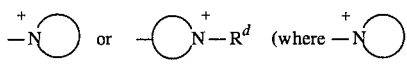

and $R^d$ are as defined hereinbefore) or (2) a group of the formula

(where $R^d$ and $R^a$ are as defined hereinbefore)

Additionally, when the benzene ring is substituted twice by the substituent $R^c$, the two substituents $R^c$, may be same or different, the preferred combination is the combination of a hydroxy group and a hydroxy group or an alkylsulfonylamino group which may be substituted, in the position ortho to the first-mentioned hydroxy group] or a salt thereof.

Referring to formula

preferred examples of

are pyrimidinium, N-methylpyrrolidinium, quinuclidinium, dihydropyrazolotriazolium and imidazolopyridazinium.

The salt of compound (Ia), (Ib) or (Ic) is preferably a pharmaceutically acceptable salt. The pharmaceutically acceptable salt includes the salts with inorganic bases, salts with organic bases, salts with inorganic acids, salts with organic acids and salts with basic or acidic amino acids. Among inorganic bases forming such salts are alkali metals (e.g. sodium, potassium, etc.) and alkaline earth metals (e.g. calcium, magnesium, etc.). The organic bases may be trimethylamine, triethylamine, pyridine, picoline, N,N'-dibenzylethylenediamine, ethanolamine, diethanolamine, tris(hydroxymethyl)aminomethane, dicyclohexylamine and so on. As said inorganic acids, there may be mentioned hydrochloric acid, hydrobromic acid, sulfuric acid, nitric acid, phosphoric acid and so on. The organic acids are formic acid,- acetic acid, trifluoroacetic acid, oxalic acid, tartaric acid, fumaric acid, maleic acid, methanesulfonic acid, benzenesulfonic acid, p-toluenesulfonic acid and so on. Among the basic or acidic amino acids mentioned above are arginine, lysine, ornithine, aspartic acid, glutamic acid and so on. Of these salts, the salts with bases (namely salts with inorganic bases, those with organic bases and those with basic amino acids) are the salts formed with the substituent carboxy groups of compounds (Ia), (Ib) and (Ic) or the salts formed when carboxy or other acidic groups are present at $R^1$, $R^a$, $R^b$ and $R^c$. The salts with acids (namely salts with inorganic acids, those with organic acids and those with acidic amino acids) are the salts formed with substituent amino groups of compounds (Ia), (Ib) and (Ic) or the salts formed when amino or other basic groups are present at $R^1$, $R^a$, $R^b$ and $R^c$.

The compounds (Ia), (Ib) and (Ic), inclusive of salts thereof, are valuable antibiotic substances having excellent activity against gram-positive and gram-negative bacteria including clinically isolated strains and can be used as safe drugs for man and domesticated animals for the prevention and treatment of infections due to various bacteria.

Further, the compounds (Ia), (Ib) and (Ic), inclusive of salts thereof, can be incorporated in animal diets as preservatives for preventing putrefaction of feed materials. Moreover, these compounds can be used as disinfectants for eliminating harmful bacteria from medical and dental apparatuses and equipment.

The compounds (Ia), (Ib) and (Ic) of the invention can be used alone or in combination with other active ingredients and, where necessary, together with pharmaceutically acceptable carriers or vehicles, with and without excipients such as stabilizers, dispersants, etc., in a variety of preparations such as capsules, tablets, liquids, e.g. solutions, suspensions, emulsions, etc., and so on. Such pharmaceutical preparations can be administered parenterally (e.g. by intravenous or intramuscular injection) or orally.

An injectable preparation can be provided in dosage units using ampules or vials containing a preservative. Such preparation may be an oily or aqueous suspension, a solution or an emulsion and may contain excipients or additives, such as known suspending agents, stabilizers and/or dispersants, in appropriate amounts. The compounds (Ia), (Ib) and (Ic), inclusive of salts thereof, can be provided in the form of powder which is to be extemporaneously dissolved in a suitable vehicle such as sterilized pyrogen-free water.

Compounds (Ia), (Ib) and (Ic), as well as salts thereof, can be admixed with a binder, such as syrup, gum arabic, gelatin, sorbitol, gum tragacanth, polyvinylpyrrolidone, etc., a filler, such as lactose, sugar, corn starch, calcium phosphate, sorbitol, glycine, etc., a lubricant, such as magnesium stearate, talc, polyethylene glycol, silica, etc., a disintegrator, such as potato starch, and/or a wetting agent, such as sodium laurylsulfate, and the resulting mixture can be processed into tablets, capsules, powders or fine powders for oral administration. Tablets, powders, etc. can be film-coated by the known methods. Preparations for oral preparation may be liquid preparations such as oily suspensions, solutions, emulsions, syrups, elixirs and so on.

There may also be incorporated, in such preparations, such other materials as the known antioxidants, preservatives, binders, wetting agents, lubricants, thickeners, flavors and so on. Furthermore, such preparations may be admixed with other active ingredients (for example, β-lactam antibiotics) to provide preparations having an extended antimicrobial spectrum.

Compounds (Ia), (Ib) and (Ic), inclusive of salts thereof, can be used as therapeutic agents for bacterial infections in the treatment and prevention of respiratory tract infection, urinary tract infection, suppurative diseases, biliary tract infection, intestinal infection, obstetric and gynecological infection, otorhinological infection, surgical infection, etc. in man and other mammals. The daily dosage of compounds (Ia), (Ib) and (Ic), inclusive of salts thereof, varies with the patient's condition and body weight, the method of administration and so on. Generally speaking, the recommended parenteral dosage for an adult patient is about 0.5 to 80 mg, preferably about 1 to 40 mg, as the active compound (compound (Ia), (Ib) or/and (Ic) or a salt thereof) per kilogram body weight per day and this amount can be administered intravenously or intramuscularly in 1–4 divided doses. The recommended daily oral dosage is about 1 to 100 mg of the active compound (compound (Ia), (Ib) or/and (Ic), or a salt thereof) per kg body weight of the adult patient, which is to be administered in 1–3 divided doses.

Compounds (Ia), (Ib) and (Ic) of the invention can be produced by known processes or processes analogous thereto. By way of illustration, compounds (Ia), (Ib) and (Ic) can be produced from compounds (IIa), (IIb) and (IIc), respectively, by subjecting the latter to cyclization reaction.

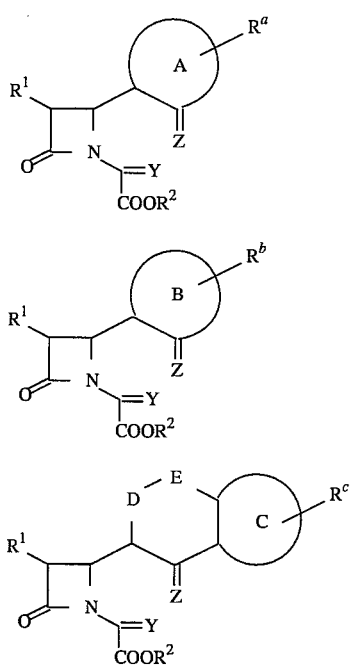

(wherein $R^1$, $R^2$, $R^a$, $R^b$, $R^c$, A, B, C, D and E are as defined hereinbefore; =Y and =Z are functional groups which may react with each other to form a double bond). The functional groups Y and Z which are necessary for the formation of a double bond and the formation reaction are known per se. [Annual Reports in Organic Synthesis 1975–1989, Academic Press, Inc. San Diego and F. A. Carey and R. J. Sundberg, Advanced Organic Chemistry Second Edition, Plenum Press, New York and London (1983)]

To be specific, a Wittig reaction (Whittig-Horner Emmons), Peterson reaction, aldol reaction involving dehydration, and McMurry reaction employing a low-valence metal can be employed.

As a preferred reaction, there may be mentioned a Witting reaction employing, for =Y and =Z, =O, =S, =Se, =P($R^5$)$_3$,

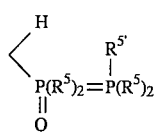

(wherein $R^5$ and $R^{5'}$ each is a lower alkyloxy, lower alkyl or aryl group). More specifically, the following production process can be employed. For convenience sake, (Ia), (Ib) and (Ic) are represented by general formula (I').

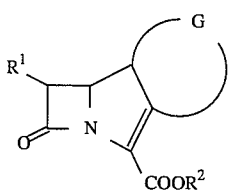

In the above formula, G is a residue forming the ring, corresponding to (Ia), (Ib) and (Ic), with positions 1 and 2 of the carbapenem ring.

Production Process 1

Compound (I') can be produced by reacting a compound of formula (II'):

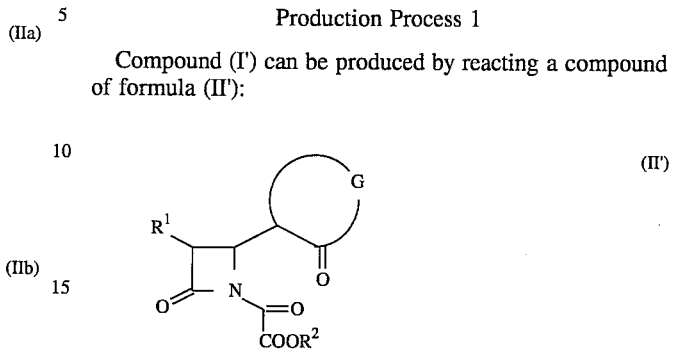

(wherein $R^1$, $R^2$ and G are as defined hereinbefore) (hereinafter referred to as compound II') with a compound of the formula (IV) or (IV')

$$P(R^5)_3 \qquad (IV),$$

$$R^{5'}P(R^5)_2 \qquad (IV')$$

(wherein $R^5$ and $R^{5'}$ are as defined hereinbefore), where necessary followed by deprotection. This reaction is generally conducted in an inert solvent under heating.

If there is a reactive group such as amino, hydroxy or carboxy in the structure of compound (II'), such group may have been protected by a suitable protective group as mentioned hereinafter.

As represented by $R^5$ and $R^{5'}$, the lower alkyloxy group may for example be methoxy, ethoxy, propoxy or butoxy, while the lower alkyl group may for example be methyl, ethyl, propyl, butyl or pentyl. The aryl group may for example be phenyl.

The inert solvent for this reaction is not particularly limited. The preferred solvents are aromatic hydrocarbons such as benzene, toluene, xylene, etc., ethers such as dioxane, diethoxyethane, tetrahydrofuran, etc. and halogenated hydrocarbons such as dichloromethane, chloroform and so on.

Preferably, compound (IV) or (IV') is used in a molar ratio of at least 2 equivalents and more preferably 2 to 10 equivalents based on compound (II'). Though it depends on the particular species of starting compounds (II') and (IV) or (IV') and solvent chosen, the reaction temperature is generally about 20° to 160° C. and preferably about 80° to 140° C. The reaction time is generally about 30 minutes to 100 hours and preferably about 1 to 72 hours.

Production Process 2

Compound (I') can be produced from a compound of the formula (II'')

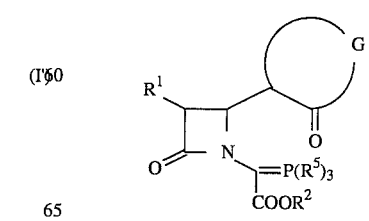

(wherein $R^1$, $R^2$, $R^5$ and G are as defined hereinbefore) by subjecting the latter to a cyclization reaction, where necessary followed by deprotection reaction. This cyclization reaction is generally carried out in an inert solvent.

When a reactive group such as amino, hydroxy or carboxy is present in the structure of compound (II''), such group may have been protected by a suitable protective group as mentioned hereinafter.

The cyclization reaction is carried out in an inert solvent at a temperature between about 0° to 160° C., preferably between about 30° to 140° C. Among the preferred inert solvents are the aromatic hydrocarbons, ethers and halogenated hydrocarbons mentioned hereinbefore. The reaction time, which depends on the species of compound (II') and the reaction temperature chosen, may range from about 30 minutes to 100 hours and generally about 1 to 72 hours.

Referring to formula (II') or (II''), where an amino group occurs in substituent $R^1$, $R^2$ or G, such amino group is preferably protected beforehand. As the protective group for such amino acid, the groups used in the field of β-lactam or peptide chemistry can be selectively utilized. Particularly preferred protective groups are formyl, chloroacetyl, phenylacetyl, phenoxyacetyl, tert-butoxycarbonyl, benzyloxycarbonyl, p-methoxybenzyloxycarbonyl, p-nitrobenzyloxycarbonyl, 2-trimethylsilylethoxycarbonyl, 2,2,2,-trichloroethoxycarbonyl, trityl, allyloxycarbonyl and so on.

Similarly, when a hydroxy group is present, such hydroxy group is preferably protected beforehand. As the protective group for such hydroxy group, there may be mentioned chloroacetyl, benzyl, p-nitrobenzyl, o-nitrobenzyl, methylthiomethyl, trimethylsilyl, triethylsilyl, tert-butyldimethylsilyl, tertbutyldiphenylsilyl, 2-tetrahydropyranyl, 4-methoxy-4-tetrahydropyranyl, p-nitrobenzyloxycarbonyl, o-nitrobenzyloxycarbonyl, allyloxycarbonyl and so on.

When a carboxy group is present, such carboxy group is preferably protected beforehand. As the protective group for carboxy, there may be employed benzyl, benzhydryl, trityl, p-methoxybenzyl, p-nitrobenzyl, o-nitrobenzyl, phenethyl, 2-trimethylsilylethyl, bis(p-methoxyphenyl)methyl, tert-butyl, allyl or the like.

In the case of compound (II) wherein =Y is =S,

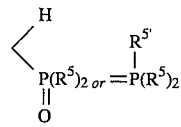

and compound (II) wherein =Z is =S, =P($R^5$)$_3$, or =Se, the compound (I') can be produced by processes analogous to the above Production Precesses 1 and 2.

The starting compound (II) for use in the present invention can be produced by processes known per se or processes analogous thereto. For example, compounds (II') and (II'') can be produced by the process illustrated in the following schema (1) or processes analogous thereto. (Schema 1)

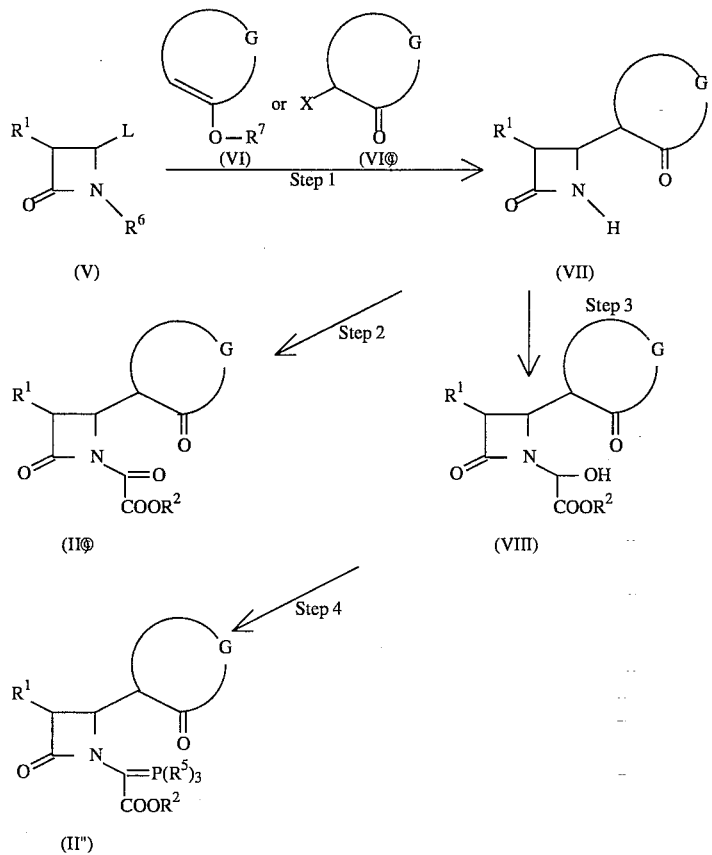

Step 1

The reaction between a compound of formula (V):

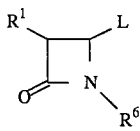

(wherein $R^1$ is as defined hereinbefore; $R^6$ is a hydrogen atom or an easily removable protective group; L is acetoxy, benzoyloxy, arylsulfonyl or lower alkylsulfonyl) and a compound of formula (VI):

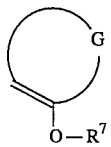

(wherein G is as defined hereinbefore; $R^7$ is an easily removable enol-protecting group) is conducted in an aprotic solvent, such as hexane, benzene, toluene, dichloromethane, chloroform, dioxane, tetrahydrofuran, acetonitrile or ether, in the presence of a Lewis acid catalyst selected from among trimethylsilyl trifluoromethanesulfonate, boron trifluoride-ether complex, zinc iodide, zinc bromide, zinc chloride, magnesium chloride, titanium tetrachloride, titanium trichloride, stannous chloride, stannic chloride, tin triflate, diethylboron triflate, ferric chloride, aluminum chloride, etc., where necessary in the presence of a nitrogen-containing base such as diisopropylethylamine, triethylamine, trimethylamine, pyridine and so on.

When compound (VI) is a substituted 2-[(trimethylsilyl)oxy- 1,3-cyclohexadiene, the preferred Lewis acid catalyst is a mixture of stannous chloride and chlorotrimethylsilane. When compound (VI) is a substituted 4-[(trimethylsily)oxy] -5,6-dihydro-2H-pyran, zinc bromide is a very suitable Lewis acid catalyst.

The reaction temperature is $-100°$ to $80°$ C.

The easily removable protective group $R^6$ in formula (V) includes, among others, organosilyl groups such as trimethylsilyl, t-butyldimethylsilyl, phenyldimethylsilyl, etc., benzyl, p-nitrobenzyl, p-methoxybenzyl, benzhydryl, 2,4-dimethoxybenzyl and so on.

The easily removable enol-protecting group $R^7$ in formula (VI) may be a protective group Which is generally used in the so-called aldol reaction (Teruaki Mukaiyama: Organic Reactions, 28, John Wiley & Sons Inc. New York, 1982). For example, trimethylsilyl, t-butyldimethylsilyl, di-n-butylboryl, dimethylboryl, diethylboryl, lithium, and compounds of the formulas $MgQ$, $ZnQ$, $AlQ_2$, $BQ_2$, $SnQ$, $ZrQ$, $Zr(cp)_2Q$ and $TiQ_3$ (where Q means F, Cl, Br, triflate, alkoxide or dialkylamide; cp means cyclopentadienyl).

The reaction between compound (V) and compound (VI')

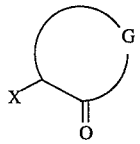

(wherein G is as defined hereinbefore; X is a halogen atom) is conducted in an aprotic solvent such as diethyl ether, tetrahydrofuran, dioxane, benzene, hexane, cyclohexane, N,N-dimethylformamide, N,N-dimethylacetamide, etc. in the presence of a metal powder or a low valence metal salt, such as zinc dust. The reaction temperature is preferably $0°$ to $100°$ C.

Following the reaction of compound (V) with compound (VI) or (VI'), the reaction product is deprotected, where necessary, to give compound (VII).

Process 2

Compound (II') can be obtained by reacting compound (VII) with a reactive derivative, such as an ester or acid halide, of an organic acid of the formula $R^2OCO—COOH$, at a temperature of $-100°$ to $80°$ C. When an acid halide is used, the reaction is preferably conducted in the presence of an acid acceptor such as an aliphatic tertiary amine, an aromatic amine or an alkali metal or alkaline earth metal carbonate or hydrogen carbonate. Preferred examples of the solvent for this reaction are the ethers and halogenated hydrocarbons mentioned hereinbefore.

Step 3

Compound (VIII) can be obtained by reacting compound (VII) with $R^2OCO—CHO$, namely glyoxylic acid or an appropriate derivative thereof, such as a hydrate, hemihydrate or a hemiacetal with, for example, a lower alkanol (e.g. methanol, ethanol, etc.). The reaction is carried out at room temperature or under heating. When a hydrate of glyoxylic acid is employed, the reaction is conducted, with the water being removed azeotropically or with an appropriate dehydrating agent. Preferably, this reaction is conducted in an appropriate inert solvent.

Step 4

Compound (II") can be obtained by treating compound (VIII) with a thionyl halide (e.g. thionyl chloride) in an appropriate solvent (such as dioxane or tetrahydrofuran) in the presence of an organic base (such as an aliphatic tertiary amine, e.g. triethylamine etc., pyridine, picoline, lutidine, etc.), if desired with cooling, to give the corresponding halide and reacting it further with a trivalent phosphorus compound of general formula (IV) in the presence of the same organic base as above. This reaction is preferably conducted in an inert solvent (such as the aforementioned ethers, halogenated hydrocarbons, and esters such as ethyl acetate, methyl acetate, etc.) at a temperature of $-10°$ to $100°$ C.

Compounds (II) other than the compounds (II') and (II") mentioned above can be produced by processes analogous to those described above as well as the processes described in Tetrahedron Letters 25, 2793 (1984).

Of the compounds (Ib) and (Ic), those compounds in which either E or D means an oxygen, sulfur or nitrogen atom can be produced by subjecting a compound of the following formula (III) or (III') to a cyclization reaction or cyclization reaction involving an extrinsic atomic group, where necessary followed by deprotection reaction. The above cyclization reaction is generally conducted in an inert solvent.

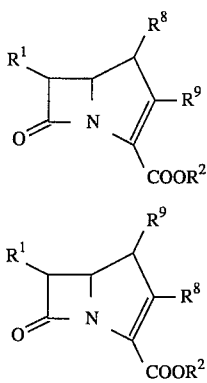

(wherein $R^1$ and $R^2$ are as defined hereinbefore; $R^8$ is a functional group selected from the class consisting of hydroxy, mercapto, amino, monosubstituted amino, carboxy and substituted hydroxycarbonyl or a lower alkyl group having said functional group and optionally being further substituted, with its carbon chain being optionally interrupted by 1 to 2 hetero-atoms selected from the group consisting of oxygen, sulfur and nitrogen; $R^9$ is a leaving group, a functional group selected from the class consisting of hydroxy, carboxy and substituted hydroxycarbonyl, or a lower alkyl group having said functional group and optionally being further substituted, with its carbon chain being optionally interrupted by hetero-atoms selected from the group consisting of oxygen, sulfur and nitrogen).

When the structural formula (III) or (III') includes a reactive group such as amino, hydroxy or carboxy, the group may be protected by a protective group mentioned above.

The leaving group $R^9$ includes, among others, chlorine, bromine, iodine, methanesulfonyloxy, trifluoromethanesulfonyloxy, benzenesulfonyloxy, toluenesulfonyloxy, diethylphosphoryloxy, diphenylphosphoryloxy and so on. The substituted hydroxycarbonyl group mentioned above includes, among others, phenyloxycarbonyl, p-nitrophenyloxycarbonyl, 2,4,6-trichlorophenyloxycarbonyl, succimidoxycarbonyl, phthalimidoxycarbonyl and so on.

The reactant which is used in the cyclization reaction involving an extrinsic atomic group includes, among others, carbonic acid derivatives such as carbonylimidazole, etc., aldehydes such as formaldehyde etc., ketones such as acetone etc., compounds each having two functional groups such as 1,2-dibromoethane, bromoacetic acid, etc., and primary amines such as methylamine and so on.

A reaction accelerator can be used to accelerate the cyclization reaction. Though dependent on the type of functional group $R^8$, $R^9$, the reaction accelerator may be an organic base such as triethylamine, diisopropylethylamine, etc., an inorganic base such as sodium hydrogen carbonate, sodium carbonate, potassium carbonate, etc., a carbodiimide compound such as N,N'-dicyclohexylcarbodiimide, N-ethyl-N'-(3-dimethylaminopropyl)carbodiimide, etc., N,N'-carbonyldimidazole, 2-chloro-1-methylpyridinium chloride, dialkyl azodicarboxylate (alkyl:ethyl, isopropyl, etc.)-triphenylphosphine, 2,2'-dipyridyl disulfide-triphenylphosphine, diphenylphosphoryl azide, diethylphosphoryl cyanide or the like.

The inert solvent for use in the cyclization reaction is selected according to the particular type of functional group $R^8$, $R^9$ and includes, among others, amides such as N,N-dimethylformamide, N,N-dimethylacetamide, etc., ethers such as tetrahydrofuran, dioxane, diethyl ether, etc., halogenated hydrocarbons such as dichloromethane, chloroform, etc., acetonitrile, esters such asmethyl acetate, ethyl acetate, etc., aromatic hydrocarbons such as benzene, toluene, etc., water and mixtures thereof.

The reaction temperature is dependent on the type of functional group $R^8$, $R^9$ and cannot be stated in general terms but to suppress side reactions, the reaction is preferably conducted at a comparatively low temperature and generally at −20° to 100° C. The reaction time is also dependent on the type of functional group $R^8$, $R^9$ and is generally in the range of 10 minutes to 72 hours.

The starting compounds (III) and (III') to be used in the present invention can be synthesized by the processes described in Japanese unexamined patent publication Nos. 69586/1982, 89285/1982, 202886/1985, 195382/1987, 303981/1988, 170378/1988 and 93586/1989 or processes analogous thereto.

The object compound thus obtained can be isolated and purified by per se known procedures such as solvent extraction, pH change, redistribution, fractional precipitation, crystallization, recrystallization, chromatography and so on. Where the product compound has protective groups, these groups can be eliminated by the routine procedures to give compound (Ia), (Ib) and (Ic) or salts thereof. The protective groups for use in the field of β-lactam synthesis or peptide synthesis have been fully explored and methods for protection and deprotection have also been well established. By way of illustration, processes involving the use of an acid, those involving the use of a base, the hydrazine method, reductive processes, the process using sodium N-methyldithiocarbamate, etc., all of which are known, can be selectively utilized.

The reaction products containing the object compound which have been produced by the processes described hereinbefore, as well as the reaction products (Ia), (Ib) and (Ic) obtained by known processes, are generally in the form of a mixture of diastereomers. Such a mixture can be fractionated into its component compounds by fractional recrystallization or column chromatography. In this specification, all references to compounds (Ia), (Ib) and (Ic) are meant to indicate such mixtures of diastereomers unless otherwise specified.

Effect of the Invention

The compounds (Ia), (Ib) and (Ic) according to the invention have a broad antibacterial spectrum and can be used in the prevention and treatment of various diseases caused by pathogenic bacteria in man and animals.

The minimal inhibitory concentrations (MIC (μg/ml)] of a representative compound of the invention were determined by the following method. Table 1 shows the results.

Assay Method

The MICs of the test compound were determined by the agar dilution method. Thus, 1.0 ml portions of serially diluted aqueous solutions of the test compound were poured in petri dishes and admixed with 9.0 ml portions of Trypticase soy agar. Then, a suspension (about $10^8$ CFU/ml) of each test strain was smeared on each agar plate and incubated at 37° C. overnight. The lowest concentration of the test compound inhibiting growth of the test strain 100% was regarded as the minimal inhibitory concentration, MIC.

| Test organism | MIC (μg/ml) 10⁸ CFU/ml Compound of Example 19 |
|---|---|
| S. aureus FDA 209P | <0.1 |
| S. aureus 308A-1 | <0.1 |
| S. aureus 1840 | 0.2 |
| S. pyogenes E-14 | <0.1 |
| S. pyogenes S-8 | <0.1 |
| S. mitis America | <0.1 |
| S. pneumoniae Type I | <0.1 |
| C. diphtheriae Tronto | 0.2 |
| E. coli NIHJ JC-2 | <0.1 |
| E. coli NIHJ O-111 | <0.1 |
| E. coli NIHJ T-7 | 1.56 |
| C. freundii IFO 12681 | 0.2 |
| C. freundii TN 474 | 6.25 |
| K. pneumoniae DT | 0.2 |
| K. oxytoca TN 1711 | 1.56 |
| E. cloacae IFO 12937 | 6.25 |
| E. cloacae TN 583 | 12.5 |
| S. marcescens IFO 12648 | 0.78 |
| P. vulgaris IFO 3988 | 0.78 |
| P. mirabilis IFO 3849 | 0.39 |
| M. morganii IFO 3168 | 0.78 |

EXAMPLES

The following reference and working examples are further illustrative of the invention. It should be understood that these are mere examples and should not be regarded as defining the scope of the invention.

The elution in the procedures of column chromatography described in Reference Examples and Examples was invariably performed under monitoring by TLC (thin-layer chromatography). The TLC monitoring was performed using Merck 60 $F_{254}$ as the TLC plate, the column chromatographic solvent as the developer, and the UV detector for detection. As the silica gel for the column, Merck 60 (70–230 or 230–400 mesh) was similarly used. As to CHP-20 resin, the product of Mitsubishi Kasei Co., Ltd. was used. The NMR spectra were recorded using a GEMINI 200 (200 MHz) spectrometer using tetramethylsilane or sodium 3-(trimethylsilyl)propionate as the internal or external standard and all the δ values were expressed in ppm. The figure presented in parentheses for any solvent system represents the ratio of component solvents by volume. All percents for solvent mixtures represent % by volume.

The symbols used in Reference Examples and Examples have the following meanings.

| | |
|---|---|
| s | singlet |
| d | doublet |
| t | triplet |
| q | quartet |
| dd | double doublet |
| ddd | double double doublet |
| ddt | double double triplet |
| m | multiplet |
| dt | double triplet |
| dq | double quartet |
| qd | quadruple doublet |
| br. | broad |
| J | coupling constant |

Reference Example 1

In dry DMF (200 ml) was dissolved 2-(2-hydroxyethyl)cyclohexanone (7.86 g) followed by addition of imidazole (9.53 g) and tert-butyldimethylchlorosilane (10 g), and the mixture was stirred at room temperature for 3 days. The reaction mixture was diluted with hexane (500 ml), washed successively with aqueous sodium hydrogen carbonate, diluted hydrochloric acid, aqueous sodium hydrogen carbonate, and aqueous sodium chloride and dried over anhydrous sodium sulfate. The solvent was then distilled off under reduced pressure and the residue was further subjected to vacuum distillation to give 7.55 g of 2-[2-(tert-butyldimethylsilyloxy)ethyl]cyclohexanone as a colorless oil.

bp 110°–115° C./0.3 mmHg

IR (Neat): 2940, 2860, 1720 cm⁻¹ ¹H-NMR (CDCl₃)δ: 0.03 (6H, s), 0.88 (9H, s), 1.3–2.5 (11H, m), 3.65 (2H, dt, J=1.6 & 6.4 Hz)

Reference Example 2

A solution of diisopropylamine (4.5 ml) in dry THF (64 ml) was cooled to −78° C., and 1.6M butyllithium in hexane (17.5 ml) was added. The mixture was stirred at 0° C. for 30 minutes. The reaction mixture was cooled to −78° C. and a solution of the compound obtained in Reference Example 1 (6.8 g) in dry THF (5 ml) was added dropwise over 10 minutes. The mixture was stirred at the same temperature for 1 hour, after which chlorotrimethylsilane (5.9 ml) was added, and the resulting mixture was further stirred at room temperature for 1 hour. The solvent was then distilled off under reduced pressure and the residue was dissolved in hexane. The solution was washed successively with aqueous sodium hydrogen carbonate, diluted hydrochloric acid, aqueous sodium hydrogen carbonate and aqueous sodium chloride and dried over anhydrous magnesium sulfate. Finally the solvent was distilled off under reduced pressure to give 9.18 g of 6-[2 -(tert-butyldimethylsilyloxy)ethyl]-1-trimethylsilyloxy- 1-cyclohexene as a colorless oil. IR (Neat): 2960, 2930, 2860, 1660 cm⁻¹ ¹H-NMR (CDCl₃)δ: 0.05 (6H, s), 0.18 (9H, s), 0.90 (9H, s), 1.3–2.2 (9H, m), 3.68 (2H, dd, J=6.1 & 7.7 Hz), 4.82 (1H, dt, J=1.2 & 3.9 Hz)

Reference Example 3

In dry dichloromethane (25 ml) were dissolved the compound obtained in Reference Example 2 (3.19 g) and (3R, 4R)-4-acetoxy-3-[(R)-1-(allyloxycarbonyloxy)ethyl] azetidin-2-one (1.29 g) followed by addition of zinc bromide (1.35 g), and the mixture was stirred at room temperature for 24 hours. The reaction mixture was then diluted with aqueous sodium hydrogen carbonate and extracted with dichloromethane. The extract was washed with aqueous sodium chloride and dried over anhydrous sodium sulfate. The solvent was then distilled off and the residue was purified by column chromatography (stationary phase: silica gel 50 g; ethyl acetatehexane 1:4) to give 1.15 g of (3S,4R)-3-[(R)-1-(allyloxycarbonyloxy)ethyl] -4-[(1S)-3-[2-(tertbutyldimethylsilyloxy)ethyl] -2-oxocyclohexan-1-yl] -azetidin-2-one (S-compound) and 0.57 g of (3S,4R)-3[ (R)-1-(allyloxycarbonyloxy)ethyl]-4-[(1R)-3-[2-(tertbutyldimethylsilyloxy)ethyl] -2-oxocyclohexan-2-yl]azetidin-2-one (R-compound), each as a colorless oil.

S-compound:IR (Neat): 2940, 2860, 1770, 1750, 1710 cm⁻¹ R-compound: IR (Neat): 2950, 2860, 1760, 1710 cm⁻¹

Reference Example 4

In dichloromethane (2.5 ml) was dissolved the (3S,4R)-3-[(R)-1-(allyloxycarbonyloxy)ethyl]-4-[(1S)-3-[ 2-(tertbutyldimethylsilyloxy)ethyl]-2-oxocyclohexan- 1-yl]azetidin-2-one (0.56 g) obtained in Reference Example 3 and while the solution was stirred, a solution of triethylamine (0.7 ml) in dichloromethane (2.5 ml) was added. Then, a solution of allyloxyoxalyl chloride (0.55 g) in dichloromethane (2.5 ml) was added dropwise at −78° C. over a period of 10 minutes. The reaction mixture was stirred at −78° C. for 5 minutes and, then, at 0° C. for 3 hours. The reaction mixture was diluted with ethyl acetate, washed with phosphate buffer (pH 7) and aqueous sodium chloride in that order and, after addition of triethylamine (0.2 ml), dried over anhydrous sodium sulfate. The solvent was then distilled off under reduced pressure and the residue was purified by flash column chromatography (stationary phase: silica gel 15 g; ethyl acetate-hexane 1:6) to give allyl [(3S,4R)-3-[(R)-1-(allyloxycarbonyloxy)ethyl] -4-[(1S)-3-[2-(tert-butyldimethylsilyloxy)ethyl] -2-oxocyclohexan-1-yl]-2-oxoazetidin-1-yl]glyoxylate.

IR (Neat): 2950, 2860, 1810, 1750, 1710, 1660 cm$^{-1}$

Reference Example 5

Starting with (3S,4R)-3-[(R)-1-(allyloxycarbonyloxy)ethyl] -4-[(1R)-3-[2-(tert-butyldimethylsilyloxy)ethyl] -2-oxocyclohexan-1-yl]azetidin-2-one, the procedure of Reference Example 4 was substantially repeated to give allyl [(3S,4R)-3-[(R)-1-(allyloxycarbonyloxy)ethyl] -4-[(1R)-3-[2-(tert-butyldimethylsilyloxy)ethyl] -2-oxocyclohexan-1-yl]-2-oxoazetidin- 1-yl]glyoxylate IR (Neat): 2940, 2860, 1815, 1755, 1710, 1660 cm$^{-1}$

Reference Example 6

In dry xylene (14 ml) were dissolved the compound obtained in Reference Example 4 (770 mg) and hydroquinone (6 mg) followed by addition of triethyl phosphite (1.2 ml) and the mixture was refluxed for 92 hours. The solvent was then distilled off under reduced pressure and the residue was purified by column chromatography (stationary phase: silica gel 20 g; ethyl acetate-hexane 1:7) to give 129 mg of allyl (5S,6R,7S)-5-[(R)-1-(allyloxycarbonyloxy)ethyl]-11-[2 -(tert-butyldimethylsilyloxy)ethyl]-4-oxo-3-azatricyclo[ 5.4.0.0$^{3,6}$]undec-1-ene-2-carboxylate as a light yellow oil.

IR (Neat): 2930, 2850, 1780, 1745, 1720, 1650 cm$^{-1}$
$^{1}$H-NMR (CDCl$_3$)δ: 0.04 (6H, s), 0.88 (9H, s), 1.3–2.2 (8H, m), 1.45 (3H, d, J=6.4 Hz), 3.0–3.1 (1H, m), 3.27 (1H, dd, J=2.8 & 8.2 Hz), 3.5–3.8 (3H, m), 3.69 (1H, dd, J=2.8 & 7.4 Hz), 4.63 (2H, dt, J=5.6 & 1.4 Hz), 4.68 (1H, ddt, J=5.6, 13.4 & 1.4 Hz), 4.79 (1H, ddt, J=5.6, 13.4 & 1.4 Hz), 5.11 (1H, dq, J=8.2 & 6.4 Hz), 5.26 (1H, dq, J=10.4 & 1.4 Hz), 5.28 (1H, dq, J=10.4 & 1.4 Hz), 5.36 (1H, dq, J=17.2 & 1.4 Hz), 5.24 (1H, dq, J=17.2 & 1.4 Hz), 5.94 (1H, ddt, J=10.4, 17.2 & 5.6 Hz), 5.97 (1H, ddt, J=10.4, 17.2 & 5° 6 Hz)

Reference Example 7

To the compound obtained in Reference Example 6 (123 mg) was added 0.25M tetrabutylammonium fluoride- 0.75M acetic acid in THF (1 ml) and the mixture was stirred at room temperature for 3 hours. The reaction mixture was diluted with ethyl acetate (20 ml), washed successively with phosphate buffer (pH 7) and aqueous sodium chloride solution and dried over anhydrous sodium sulfate. The solvent was then distilled off under reduced pressure and the residue was purified by column chromatography (stationary phase: silica gel 10 g; ethyl acetate-hexane 1:1) to give 83 mg of allyl (5S,6R,7S)-5-[(R)-1-(allyloxycarbonyloxy)ethyl]-11-(2 -hydroxyethyl)-4-oxo-3-azatricyclo[5.4.0.0$^{3,6}$]undec-1 -ene-2-carboxylate as a light yellow oil.

IR (Neat): 3500, 2930, 2850, 1775, 1740, 1715 cm$^{-1}$
$^{1}$H-NMR (CDCl$_3$)δ: 1.44 (3H, d, J=6.4 Hz), 1.3–2.2 (9H, m), 2.9–3.1 (1H, m), 3.29 (1H, dd, J=2.8 & 8.0 Hz), 3.4–3.7 (3H, m), 3.74 (1H, dd, J=2.8 & 7.4 Hz), 4.63 (2H, dt, J=5.4 & 1.4 Hz), 4.71 (1H, ddt, J=5.4, 13.6 & 1.4 Hz), 4.83 (1H, ddt, J=5.4, 13.6 & 1.4 Hz), 5.12 (1H, dq, J=8.1 & 6.4 Hz), 5.2–5.5 (4H, m), 5.94 (1H, ddt, J=10.4 17.2 & 5.4 Hz), 5.98 (1H, ddt, J=10.4, 17.2 & 5.4 Hz)

Reference Example 8

Using the compound obtained in Reference Example 5, the procedure of Reference Example 6 was substantially repeated to give allyl (5S,6R,7S)-5-[(R) -1-(allyloxycarbonyloxy)ethyl]-11-[2-(tert-butyldimethylsilyloxy)ethyl] -4-oxo-3-azatricyclo[5.4.0.0$^{3,6}$]undec-1-ene-2-carboxylate.

IR (Neat): 2940, 2860, 1780, 1745, 1720, 1660 cm$^{-1}$
$^{1}$H-NMR (CDCl$_3$)δ: 0.02 (6H, s), 0.88 (9H, s), 1.3–2.0 (8H, m), 1.45 (3H, d, J=6.2 Hz), 3.0–3.2 (1H, m), 3.34 (1H, dd, J=3.0 & 8.2 Hz), 3.4–3.8 (3H, m), 4.10 (1H, dd, J=3.0 & 10 Hz), 4.6–4.9 (4H, m), 5.12 (1H, dq, J=8.2 & 6.4 Hz), 5.2–5.5 (4H, m), 5.94 (1H, ddt, J=10.4, 17.2 & 5.4 Hz), 5.97 (1H, ddt, J=10.4, 17.2 & 5.4 Hz)

Reference Example 9

Using the compound obtained in Reference Example 8, the procedure of Reference Example 7 was otherwise repeated to give allyl (5S,6R,7S)-5-[(R)-1-(allyloxycarbonyloxy)ethyl] -11-(2-hydroxyethyl)-4-oxo-3-azatricyclo[ 5.4.0.0$^{3,6}$]undec-1-ene-2-carboxylate.

IR (Neat): 3500, 2920, 2850, 1775, 1740, 1710 cm$^{-1}$
$^{1}$H-NMR (CDCl$_3$)δ: 1.3–2.0 (SH, m), 1.45 (3H, d, J=6.4 Hz), 2.72 (1H, dd, J=4.3 & 9.1 Hz), 3.00 (1H, ddd, J=5.0, 10.4 & 12.4 Hz), 3.38 (1H, dd, J=3.2 & 7.8 Hz), 3.4–3.8 (3H, m), 4.14 (1H, dd, J=3.2 & 10.4 Hz), 4.63 (2H, dt, J=5.4 & 1.4 Hz), 4.69 (1H, ddt, J=5.4, 13.6 & 1.4 Hz), 4.83 (1H, ddt, J=5.4, 13.6 & 1.4 Hz), 5.13 (1H, dq, J=7.8 & 6.4 Hz), 5.2–5.3 (2H, m), 5.36 (1H, dq, J=17.2 & 1.4 Hz), 5.48 (1H, dq, J=17.2 & 1.4 Hz), 5.94 (1H, ddt, J=10.4, 17.2 & 5.4 Hz), 5.99 (1H, ddt, J=10.4, 17.2 & 5.4 Hz)

Reference Example 10

Using (3R,4R)-4-acetoxy-3-[(R)-1-(allyloxycarbonyloxy)ethyl] azetidin-2-one and 1,2-bis(trimethylsilyloxy)-2-cyclohexene, the procedure of Reference Example 3 was otherwise repeated to give (3S,4R)-3-[(R)-1-(allyloxycarbonyloxy)ethyl]-4-[ (1S,3R)-2-oxo-3-trimethylsilyloxycyclohexan-1-yl] azetidin-2-one (S-compound) and (3S,4R)-3-[(R)-1-(allyloxycarbonyloxy)ethyl] -4-[(1R,3S)-2-oxo-3-trimethylsilyloxycyclohexan- 1-yl]azetidin-2-one (R-compound), each as a colorless oil.

R-compound: IR (Neat): 3300, 2940, 1770–1720, 1370, 1250 cm$^{-1}$ S-compound: IR (Neat): 3340, 2940, 1770, 1740, 1710, 1250 cm$^{-1}$

Reference Example 11

Using the (3S,4R)-3-[(R)-1-(allyloxycarbonyloxy)ethyl] -4-[(1S,3R)-2-oxo-3-trimethylsilyloxycyclohexan- 1-yl] azetidin-2-one obtained in Reference Example 10, the procedure of Reference Example 4 was otherwise repeated to give allyl [(3S,4R)-3-[(R)-1-(allyloxycarbonyloxy)ethyl] -4-[(1S,3R)-3-[2-oxo-3 -trimethylsilyloxycyclohexan-1-yl]- 2-oxoazetidin-1-yl] glyoxylate.

IR (Neat): 2950, 1810, 1750, 1710, 1450, 1380, 1255 cm$^{-1}$

Reference Example 12

Using the (3S,4R)-3-[(R)-1-(allyloxycarbonyloxy)ethyl]-4-[(1R,3S)-2-oxo-3-trimethylsilyloxycyclohexan-1-yl]azetidin-2-one obtained in Reference Example 10, the procedure of Reference Example 4 was otherwise repeated to give allyl [(3S,4R)-3-[(R)-1-(allyloxycarbonyloxy)ethyl]-4-[(1R,3S)-3-[2-oxo-3-trimethylsilyloxycyclohexan-1-yl]-2-oxoazetidin-1-yl]glyoxylate IR (Neat): 2950, 1810, 1755, 1710, 1700, 1260 cm$^{-1}$

Reference Example 13

To a suspension of 6-allyloxycarbonylamino-1,2,3,4-tetrahydro-1-naphthalenone (9.81 g) in dichloromethane (80 ml) was added a solution of triethylamine (12.3 ml) in dichloromethane-(20 ml) and a solution of trimethylsilyl trifluoromethanesulfonate (18.6 ml) in dichloromethane (20 ml) in the order mentioned, and the mixture was stirred with ice-cooling for 2 hours and, then, at room temperature for 2 hours. Then, a solution of (3R,4R)-4-acetoxy-3-[(R)-[1-tert-butyldimethylsilyl)oxy] ethyl]azetidin-2-one (11.5 g) in dichloromethane (25 ml) was added dropwise with ice cooling. The reaction mixture was stirred with ice cooling for 1 hour and after addition of saturated aqueous solution of sodium hydrogen carbonate, further stirred at the same temperature for 1.5 hours. The organic layer was separated and the aqueous layer was extracted with dichloromethane. The organic layers were combined, dried over anhydrous magnesium sulfate and concentrated under reduced pressure. The residue was dissolved in THF-water (4:1, 100 ml) followed by addition of pyridinium p-toluenesulfonate (503 mg). The mixture was stirred at room temperature for 1.5 hours, after which THF was distilled off under reduced pressure. The residue was extracted with dichloromethane and the extract was washed with aqueous sodium chloride solution and dried over anhydrous magnesium sulfate. The solvent was then distilled off under reduced pressure and the solid residue was dissolved in dichloromethane. The precipitate formed upon addition of hexane was collected by filtration and washed with ether to give 12.5 g of (3S,4R)-4-[(RS)-6-allyloxycarbonylamino-1,2,3,4-tetrahydro-1-oxonaphthalen-2-yl]-3-[(R)-1-[(tert-butyldimethylsily-1)oxy]ethyl]azetidin-2-one as a light brown solid.

m.p. 192°–193° C. IR (KBr): 3340, 3250, 2955, 2940, 2855, 1740, 1715 1680, 1670, 1590, 1540 cm$^{-1}$

Reference Example 14

In benzene (150 ml) were dissolved the compound obtained in Reference Example 13 (4.73 g) and allyl glyoxylate (1.94 g), and the solution was refluxed for 12 hours with the byproduct water being removed with a Dean-Stark trap. The reaction mixture was concentrated under reduced pressure and the residue was purified by column chromatography (stationary phase: silica gel 100 g; ethyl acetate-hexane 1:3) to give 5.4 g of allyl 2-[ (3S,4R)-4-[(RS)-6-allyloxycarbonylamino-1, 2,3,4 -tetra-hydro-1-oxonaphthalen-2-yl]-3-[(R)-1-[(tertbutyldimethylsilyl)oxy]ethyl]-2-oxoazetidin-1-yl]-2-hydroxyacetate as a colorless oil.

IR (Neat): 3450, 3330, 2950, 2855, 1750, 1670, 1600, 1540 cm$^{-1}$ $^1$H-NMR (CDCl$_3$)δ:0.06–0.09 (6H, m), 0.85–0.87 (9H, m), 1.23–1.34 (3H, m), 1.71–3.12 (5H, m), 3.68–4.83 (6H, m), 5.07–6.09 (7H, m), 6.90–6.93 (1H, m), 7.13–7.20 (1H, m), 7.47–7.53 (1H, m), 7.88–8.00 (1H, m)

Reference Example 15

To a solution of the compound obtained in Reference Example 14 (5.40 g) in THF (20 ml) was added 2,6-lutidine (2.22 ml) and, then, a solution of thionyl chloride (1.04 ml) in THF (3 ml) was added dropwise at −78° C. The reaction mixture was stirred at the same temperature for 15 minutes and, then, at 0° C. for 30 minutes, after which it was concentrated under reduced pressure. To the residue was added toluene, and the resulting precipitate was separated and washed with toluene. The filtrate was concentrated under reduced pressure and the residue was dissolved in THF (50 ml). To this solution were added 2,6-lutidine (2.22 ml) and triphenylphosphine (4.88 g), and the mixture was stirred at room temperature for 4 days. The solvent was then distilled off under reduced pressure and the residue was dissolved in ethyl acetate, washed with water and saturated aqueous solution of copper sulfate and dried over anhydrous magnesium sulfate. After concentration under reduced pressure, the residue was purified by column chromatography (stationary phase: silica gel 130 g; ethyl acetate-hexane 1:2) to give 6.00 g of ally 2-[(3S,4R)-4-[(RS)-6 -allyloxycarbonylamino-1,2,3,4-tetrahydro-1-oxo -naphthalen-2-yl]-3-[(R)-1-[(tert-butyldimethylsilyl)oxy] ethyl]-2-oxoazetidin-1-yl]-2-triphenylphosphorideneacetate as a light brown amorphous solid.

IR (KBr): 3440, 3270, 2950, 2930, 2850, 1740, 1670, 1605, 1590, 1540, 1440 cm$^{-1}$ $^1$H-NMR (CDCl$_3$)δ:0.16–0.05 (6H, m), 0.69–0.80 (9H, m), 1.07–1.09 (3H, m), 2.02–3.18 (6H, m), 3.45–6.08 (12H, m), 6.97–8.01 (19H, m)

Reference Example 16

In methanol (72 ml) was dissolved the compound obtained in Reference Example 15 (6.00 g) followed by addition of 2N-hydrochloric acid (7.2 ml). The mixture was stirred at room temperature for 23 hours, after which saturated sodium hydrogen carbonate solution was added. The methanol was distilled off under reduced pressure and the residue was diluted with water and extracted with ethyl acetate. The extract was washed with aqueous sodium chloride solution, dried over anhydrous sodium sulfate and concentrated under reduced pressure. The residue was purified by column chromatography (stationary phase: silica gel 100 g; ethyl acetate-hexane 2:1) to give 5.10 g of allyl 2-[(3S,4R)-4-[(RS)-6-allyloxycarbonylamino-1,2,3,4 -tetrahydro-1-oxonaphthalen-2-yl]-3-[(R)-1-hydroxyethyl]-2-oxoazetidin-1-yl]-2-triphenylphosphorideneacetate as a light yellow amorphous solid.

IR (Kbr): 3430, 3260, 3060, 2935, 1740, 1540 cm$^{-1}$ $^1$H-NMR (CDCl$_3$)δ: 1.08–1.11 (3H, m), 2.53–3.21 (6H, m), 4.00–5.45 (10H, m), 5.82–6.03 (2H, m), 7.05–7.90 (19H, m)

Reference Example 17

The procedure of Reference Example 13 was substantially repeated to give (RS)-1-(allyloxycarbonyl)-2-[ (2S,3S)-3-[(R)-1-[(tert-butyldimethylsilyl)oxy]ethyl]- 4-oxoazetidin-2-yl]piperidin-3-one.

IR (Neat): 3280, 2950, 2930, 2860, 1760, 1705, 1650, 1408 cm$^{-1}$

Reference Example 18

To a solution of the compound obtained in 10 Reference Example 17 (4.55 g) in acetonitrile (20 ml) was added boron trifluoride etherate (2.84 g) and the mixture was stirred at 0° C. for 2 hours. To this solution were added a saturated aqueous solution of sodium hydrogen carbonate (50 ml) and ethyl acetate (100 ml) and the mixture was stirred for 30 minutes. The aqueous layer was extracted with ethyl acetate and the organic layer was dried over anhydrous sodium sulfate. The solvent was then distilled off under reduced pressure and the residue was purified by flash column chromatography (stationary phase: silica gel 50 g: eluent: ethyl acetate) to give (RS)-1-(allyloxy-carbonyl)- 2-[(2S, 3S)-3-[(R)-1-hydroxyethyl]-4-oxoazetidin -2-yl]piperidin-3-one. This product was dissolved in dichloromethane (30 ml), followed by addition of chlorotrimethylsilane (4.44 g) and pyridine (3.76 g) at 0° C., and the mixture was stirred for 2 hours. The solvent was then distilled off under reduced pressure and ether (200 ml) was added to the residue. The organic layer was washed successively with saturated aqueous solution of copper sulfate and aqueous sodium chloride solution and dried over anhydrous sodium sulfate. The solvent was then distilled off under reduced pressure. To the residue were added ethyl acetate-methanol (1:1, 50 ml) and silica gel (15 g) and the mixture was stirred for 4 hours. The silica gel was filtered off and the filtrate was concentrated under reduced pressure. Finally the residue was purified by flash column chromatography (stationary phase: silica gel 80 g; eluent: ethyl acetate-hexane 2:3) to give (RS)-1-(allyloxycarbonyl)-2-[(2S,3S)-3-[ (R)-1-(trimethylsilyloxy)ethyl]-4-oxoazetidin-2-yl] -piperidin-3-one (3.30 g).

IR (Neat): 3275, 2950, 2900, 1760, 1703, 1648, 1412 $cm^{-1}$

Reference Example 19

To a solution of the compound obtained in Reference Example 18(1.07 g) in dichloromethane (10 ml) was added a solution of pyridine (656 mg) in dichloromethane (2 ml) at 0° C., followed by addition of a solution of p-nitrobenzyl chloroglyoxylate (1.34 g) in dichloromethane (5 ml). The mixture was stirred for 2 hours, after which ethanol (255 mg) was added. The mixture was stirred for 20 minutes and ether (50 ml) was added. The organic layer was washed successively with water, saturated aqueous solution of copper sulfate and aqueous sodium chloride solution and dried over anhydrous sodium sulfate. The solvent was distilled off under reduced pressure and the residue was purified by flash column chromatography (stationary phase: silica gel 15 g; eluent: ethyl acetate-hexane 2:7) to give p-nitrobenzyl (2S, 3S)-2-[(RS)-1 -(allyloxycarbonyl)-3-oxopiperidin-2-yl]-3-[(R)-1-(trimethylsilyloxy)ethyl] -4-oxoazetidin-1-yl]glyoxylate (1.00 g).

IR (Neat): 2950, 2900, 1810, 1760, 1700, 1650, 1605, 1520 $cm^{-1}$

Reference Example 20

Using the compound obtained in Reference Example 19, the reaction procedure of Reference Example 6 was otherwise repeated to give p-nitrobenzyl (5S,6S,7S)-8 -(allyloxycarbonyl)-5-[(R)-1-(trimethylsilyloxy)ethyl] -4-oxo-3,8-diazatricyclo[5.4.0.0$^{3,6}$]undec-1-ene-2 -carboxylate (S-compound) and p-nitrobenzyl (5S,6S,7R)- 8-(allyloxycarbonyl)-5-[(R)-1-(trimethylsilyloxy)ethyl] -4-oxo-3,8-diazatricyclo[5.4.0.0$^{3,6}$ -undec-1-ene-2-carboxylate (R-compound).

S-compound: IR (Neat): 2950, 1780, 1705, 1640, 1600, 1520 $cm^{-}$ R-compound: IR (Neat): 2950, 1775, 1705, 1645, 1605, 1520 $cm^{-1}$ Reference Example 21

Using the p-nitrobenzyl (5S,6S,7R)-8-(allyloxycarbonyl) -5-[(R)-1-(trimethylsilyloxy)ethyl]-4-oxo- 3,8-diazatricyclo [5.4.0.0$^{3,6}$]undec-1-ene-2-carboxylate obtained in Reference Example 20, the reaction procedure of Reference Example 45 was substantially repeated to give p-nitrobenzyl (5S,6S,7R)-8 -(allyloxycarbonyl)-5-[(R)-1-hydroxyethyl]-4-oxo-3,8-diazatricyclo[ 5.4.0.0$^{3,6}$]-Undec-1-ene-2-carboxylate.

IR (Neat): 3460, 2950, 1765, 1720, 1693, 1610, 1523 $cm^{-1}$

Reference Example 22

In benzene (100 ml) was dissolved tetrahydropyran-3-one (35.1 g) followed by addition of cyclohexylamine (40 ml) with ice-cooling the mixture was-stirred at the same temperature for 30 minutes and, then, refluxed for 1 hour, with the byproduct water being distilled off. After cooling to room temperature, the reaction mixture was added dropwise to 1.6M n-butyllithium in hexane (230 ml) in dry THF (350 ml) with ice-cooling over 30 minutes and the mixture was stirred at the same temperature for 30 minutes. Then, a solution of 2 -(tert-butyldimethylsilyloxy)ethyl iodide (75 g) in THF (140 ml) was added with ice-cooling over 20 minutes and the mixture was stirred at the same temperature for 1 hour. Then, 10% aqueous solution of citric acid (1 l) was added and the mixture was vigorously stirred. This reaction mixture was shaken with hexane (3 l) and the organic layer was separated. The organic layer was washed with water and aqueous sodium chloride solution in that order, and dried over anhydrous magnesium sulfate. The solvent was then distilled off under reduced pressure and the residue was purified by column chromatography (stationary phase: silica gel 1 kg; ethyl acetate-hexane 1:10) to give 42.8 g of 4-[2 -(tert-butyldimethylsilyloxy)ethyl]-3-oxotetrahydropyran as light yellow oil.

IR (Neat): 2960, 2930, 2850, 1720 $cm^{-1}$

Reference Example 23

The compound obtained in Reference Example 22 was reacted in the same manner as described in Reference Example 2 and 3 to give (3S,4S)-3-[(R)-1-(allyloxycarbonyloxy)ethyl] -4-[(2R)-4-[2-(tert-butyldimethylsilyloxy)ethyl] -3-oxotetrahydropyran-2-yl] azetidin-2-one.

IR (Neat): 2950, 2920, 2850, 1760, 1750 $cm^{-1}$

Reference Example 24

The compound obtained in Reference Example 23 was reacted in the same manner as described in Reference Examples 14 and 15 to give allyl 2-[(3S,4S)-3-[(R)-1-(allyloxycarbonyloxy)ethyl] -4-[(2R)-4[2-(tertbutyldimethylsilyloxy)ethyl] -3-oxotetrahydropyran-2-yl] -2-oxoazetidin-1-yl]-2-triphenylphosphorideneacetate.

IR (KBr): 3050, 2950, 2930, 2850, 1750, 1640, 1620 $cm^{-1}$

Reference Example 25

To a solution of diisopropylamine (0.294 ml) in dry THF (5 ml) was added butyllithium (1.25 ml, 1.6M in hexane) dropwise at 0° C. and the mixture was stirred for 10 minutes. This solution was cooled to −78° C. and a solution of (3S,4S)-1-(tert-butyldimethylsilyl)-3-[(R)- 1-(tert-butyldimethylsilyloxy)ethyl]-4-[(2RS)-3 -oxotetrahydropyran-2-yl)azetidin-2-one (441 mg) in dry THF (2 ml) was added dropwise. The mixture was stirred for 30 minutes, after which trimethylchlorosilane (0.267 ml) was added. This mixture was stirred at −20° C. for 10 minutes. The reaction mixture was then poured in a saturated aqueous solution of ammonium chloride (20 ml) and extracted with ether (20 ml). The organic layer was washed successively with water (20 ml), 2% HCl (20 ml), saturated aqueous sodium hydrogen carbonate (20 ml) and saturated aqueous sodium chloride (20 ml). The extract was then dried over anhydrous magnesium sulfate and the solvent was distilled off under reduced pressure. Finally, the residue was purified by silica gel column chromatography (230–400 mesh, 26 g; ethyl acetate-hexane=1:15) to give (3S,4S)-1-(tert-butyldimethylsilyl)-3-[(R)-1-(tert-butyldimethylsilyloxy)ethyl] -4-[(2R)-3 -trimethylsilyloxy-5,6-dihydropyran-2-yl]azetidin-2-one (228 mg) as a colorless oil.

IR (neat): 2955, 2925, 2895, 2855, 1745, 1665 cm$^{-1}$.
$^1$H-NMR (200 MHz, CDCl$_3$)δ: 0.06 (3H, s), 0.07 (3H, s), 0.21 (9H, s), 0.22 (3H, s), 0.23 (3H, s), 0.89 (9H, s), 0.96 (9H, s), 1.18 (3H, d, J=6.2 Hz), 2.00–2.35 (2H, m), 3.27 (1H, dd, J=5.3 Hz and 2.3 Hz), 3.56 (1H, ddd, 11.0 Hz, 6.8 Hz and 2.4 Hz), 3.86 (1H, dd, J=11.0 Hz and 5.2 Hz), 3.85–3.95 (2H, m), 4.14 (1H, dd, J=6.2 Hz and 5.3 Hz), 4.96 (1H, t, J=4.0 Hz)

Reference Example 26

The compound obtained in Reference Example 25 (400 mg) was dissolved in dry hexane (5 ml). Then, m-chloroperbenzoic acid (480 mg) was added at 0° C. and the mixture was stirred at the same temperature for 2 hours. This solution was poured in a 5% aqueous solution of sodium sulfite and the mixture was stirred for 30 minutes. The reaction mixture was extracted with ethyl acetate and the organic layer was washed with saturated aqueous sodium hydrogen carbonate and saturated aqueous sodium chloride in that order. The extract was dried over anhydrous magnesium sulfate and the solvent was distilled off under reduced pressure. The residue was dissolved in THF-water (4:1, 10 ml) followed by addition of pyridinium p-toluenesulfonate (40 mg) and the mixture was stirred at room temperature for 1.5 hours. The solvent was then distilled off under reduced pressure and the residue was diluted with ethyl acetate, washed with water and saturated aqueous sodium chloride solution in that order and dried over anhydrous magnesium sulfate. The solvent was then distilled off under reduced pressure and the residue was subjected to silica gel column chromatography (230–400 mesh, 25 g; ethyl acetate-hexane=1:4) to give (3S,4S)-1-(tert-butyldimethylsilyl)-3-[(R)-1-(tert-butyldimethylsilyloxy)ethyl] -4-[(2R,4S)-4-hydroxy-3 -oxotetrahydropyran-2-yl]azetidin-2-one (S-Compound) (94 mg) and (3S,4S)-1-(tert-butyldimethylsilyl)-3-[(R)-1 -(tert-butyldimethylsilyloxy)ethyl]-4-[(2R,4R)-4 -hydroxy-3-oxotetrahydropyran-2-yl]azetidin-2-one (R-compound) (167 mg), each as a colorless oil.

S-compound: IR (neat): 3400, 2950, 2930, 2880, 2855, 1740 cm$^{-1}$. $^1$H-NMR (200 MHz, CDCl$_3$)δ: 0.05 (3H, s), 0.07 (3H, s), 0.21 (3H, s), 0.28 (3H, s), 0.88 (9H, s), 0.95 (9H, s), 1.02 (3H, d, J=6.4 Hz), 1.82–2.05 (1H, m), 2.57–2.75 (1H, m), 3.15 (1H, dd, J=3.8 Hz and 2.8 Hz), 3.82 (1H, ddd, J=12.0 Hz, 6.6 Hz and 5.0 Hz), 3.90 (1H, dd, J=8.4 Hz and 2.8 Hz), 4.11 (1H, d, J=8.4 Hz), 4.03–4.45 (2H, m), 4.50 (1H, d, J=11.2 Hz and 8.4 Hz)

R-compound: IR (neat): 3420, 2950, 2930, 2880, 2855, 1740 cm$^{-1}$. $^1$H-NMR (200 MHz, CDCl$_3$)δ: 0.06 (3H, s), 0.09 (3H, s), 0.18 (3H, s), 0.21 (3H, s), 0.89 (3H, s), 0.95 (3H, s), 1.28 (3H, d, J=6.4 Hz), 2.09 (1H, dq like, J=12.6 Hz and 5.0 Hz), 2.57 (1H, ddt, J=13.0 Hz, 7.4 Hz and 2.0 Hz), 2.93 (1H, dd, J=4.2 Hz and 1.4 Hz), 3.79 (1H, td, J=12.2 Hz and 2.0 Hz), 3.83–3.87 (2H, m), 4.10 (1H, ddd, J=12.2 Hz, 5.0 Hz and 2.0 Hz), 4.29 (1H, qd, J=6.4 Hz and 4.2 Hz), 4.31 (1H, dd, J=12.2 Hz and 7.4 Hz)

Reference Example 27

The R-compound obtained in Reference Example 26 was dissolved in dry DMF (3 ml) followed by addition of imidazole (625 mg) and tert-butyldimethylsilyl chloride (691 mg), and the mixture was stirred at room temperature for 4 hours. The reaction mixture was diluted with water and extracted with ether. The organic layer was washed with saturated aqueous sodium chloride solution and dried over anhydrous magnesium sulfate. The solvent was then distilled off under reduced pressure and the residue was subjected to silica gel column chromatography (70–230 mesh, 30 g; ethyl acetate-hexane =1:9) to give (3S,4S)-1-(tert -butyldimetylsilyl)-3-[(R)-1-(tert-butyldimethylsilyloxy)ethyl] -4-[(2R,4R)-4-(tert-butyldimethylsilyloxy)- 3-oxotetrahydropyran-2-yl]azetidin-2one (1.028 g).

IR (KBr): 2955, 2930, 3880, 2855, 1740, 1725$^{-1}$.

Reference Example 28

The compound obtained in Reference Example 27 (1.435 g) was dissolved in methanol (60 ml) and after the solution was cooled to 0° C. potassium fluoride (160 mg) was added. The mixture was stirred at the same temperature for 2 hours. The reaction mixture was then diluted with saturated aqueous solution of sodium hydrogen carbonate and extracted with ethyl acetate. The organic layer was washed with saturated aqueous solution of sodium chloride and dried over anhydrous magnesium sulfate. The solvent was then distilled off under reduced pressure and the residue was subjected to silica gel column chromatography (70–230 mesh, 50 g; ethyl acetate-hexane=1:9) to give (3S,4S)-3-[(R)-1 -(tert-butyldimethylsilyloxy)ethyl]-4-[(2R,4R)-4- (tert -butyldimethylsilyloxy)-3-oxotetrahydropyran-2-yl] azetidin-2-one (591 mg)

IR (neat): 2954, 2929, 2885, 2856, 1770, 1749 cm$^{-1}$.

Reference Example 29

The compound obtained in Reference Example 28 was reacted as in Reference Examples 14, 15 and 16 to give allyl 2-[(3S,4S)-3-[(R)-1-hydoxyethyl]-4-[(2R,4S)-4 -hydroxy-3-oxotetrahydropyran-2-yl]-2-oxoazetidin-1-Yl]- 2-triphenylphosphoridene acetate.

IR (KBr): 3421, 1750, 1734, 1653, 1616 cm$^{-1}$.

Reference Example 30

The S-compound obtained in Reference Example 26 was reacted as in Reference Examples 27 and 28 to give (3S, 4S)-3-[(R)-1-(tert-butyldimethylsilyloxy)ethyl]-4-[ (2R, 4S)-4-(tert-butyldimethylsilyloxy)-3 -oxotetrahydropyran-2-yl]azetidin-2-one IR (neat): 3445, 2954, 2929, 2585, 2858, 1749 cm$^{-1}$.

Reference Example 31

The compound obtained in Reference Example 30 was reacted as in Reference Example 14 to give allyl 2-[ (3S, 4S)-3-[(R)-1-(tert-butyldimethylsilyloxy)ethyl]-4-[ (2R, 4S)-4-(tert-butyldimethylsilyloxy)-3 -oxotetrahydropyran-2-yl]-2-oxoazetidin-1-yl]-2-hydroxyacetate.

IR (neat): 3439, 2954, 2929, 2885, 2858, 1765, 1745$^{-1}$.

Reference Example 32

2-[(tert-Butyldimethylsilyloxy)methyl]cyclohexanone was reacted as in Reference Example 2 to give 6-[(tert-butyldimethylsilyloxy)methyl]-1-trimethylsilyloxy-1-cyclohexene.

IR (neat): 2950, 2930, 2850, 1660, 1250 cm$^{-1}$.

Reference Example 33

The compound obtained in Reference Example 32 was reacted as in Reference Example 3 and purified to give (3S,4R)-3-[(R)-1-(allyloxycarbonyloxy)ethyl]-4-[(1R,3R)-3-(tert-butyldimethylsilyloxy)methyl-2-oxocyclohexan-1-yl]azetidin-2-one.

IR (neat): 3270, 2930, 2850, 1770–1730 cm$^{-1}$. $^1$H-NMR (200 MHz, CDCl$_3$)δ: 0.04 (6H, s), 0.86 (9H, s), 1.43 (3H, d, J=6.3 Hz), 1.53–2.13 (6H, m), 2.53–2.77 (2H, m), 3.07 (1H, dd, J=2.4 Hz), 3.76 (1H, dd, J=10.1 Hz, J=6.6 Hz), 3.90 (1H, dd, J=10.1 Hz, J=7.0 Hz), 3.99 (1H, dd, J=5.7 Hz, J=2.4 Hz), 4.53–4.71 (2H, m), 5.10 (1H, m), 5.24–5.41 (2H, m), 5.84–6.03 (2H, m)

Reference Example 34

The compound obtained in Reference Example 33 was reacted as in Reference Examples 14, 15 and 16 to give allyl 2-[(3S, 4R)-3-[(R)-1-(allyloxycarbonyloxy)ethyl]-4-[(1R, 3R)-3-hydroxymethyl-2-oxocyclohexan-1-yl]-2-oxoazetidin-1-yl]-2-triphenylphosphorideneacetate.

IR (neat): 2930, 1745, 1250 cm$^{-1}$.

Reference Example 35

A solution of the compound obtained in Reference Example 34 (1.96 g) in toluene (70 ml) was refluxed for 8 hours. The reaction mixture was concentrated to dryness and the residue was subjected to silica gel column chromatography (70–230 mesh, 40 g; ethyl acetate-hexane=1:2) to give 800 mg of allyl (5S,6R,7S,11S)-5-[(R)-1-(allyloxycarbonyloxy)ethyl]-11-hydroxymethyl-4-oxo-3-azatricyclo [5.4.0.0$^{3,6}$]undec-1-ene-2-carboxylate as a colorless oil.

IR (neat): 3480, 2930, 1780, 1745, 1720 cm$^{-1}$. $^1$H-NMR (200 MHz, CDCl$_3$)δ: 1.24–2.05 (6H, m), 1.45 (3H, d, J=6.3 Hz!), 3.08 (1H, m), 3.39 (1H, dd, J=7.9 Hz, J=3.3 Hz), 3.74–3.81 (3H, m), 4.17 (1H, dd, J=10.5 Hz, J=3.3 Hz), 4.61–4.87 (4H, m), 5.12 (1H, m), 5.23–5.51 (4H, m), 5.84–6.07 (2H, m)

Reference Example 36

In an argon atmosphere, a solution of n-butyllithium in hexane (1.41M, 8.94 ml) was added dropwise to a solution of diisopropylamine (2.02 ml=1.60 g) in THF (79 ml) at −78° C. The mixture was stirred under ice-cooling for 15 minutes, after which it was cooled to −78° C. Then, a solution of (3S,4S)-3-[(R)-1-(allyloxycarbonyloxy)ethyl]-4-[(2R)-3-oxote-trahydropyran-2-yl]-1-trimethylsilylazetidin-2-one (3.88 g) in THF (25 ml) was added dropwise at the same temperature. The mixture was stirred at the same temperature for 15 minutes, after which chlorotrimethylsilane (1.72 g, 15.8 mmol) was added dropwise and the mixture was stirred with ice-cooling for 15 minutes. To this reaction mixture was added a saturated aqueous solution of NaHCO$_3$ (100 ml) and the mixture was stirred well and extracted with ether. The organic layers were pooled, washed with water and saturated aqueous solution of sodium chloride and dried over anhydrous magnesium sulfate. The solvent was removed under reduced pressure and the residue was dissolved in THF (80 ml) followed by addition of NaHCO$_3$ (100 mg). Then, a solution of N-bromosuccinimide (1.96 g) in THF (50 ml) was added dropwise with ice-cooling. The mixture was stirred at the same temperature for 15 minutes, after which it was diluted with a saturated aqueous solution of NaHDO$_3$ (100 ml) and extracted with ether. The organic layers were combined, washed with water and saturated aqueous solution of sodium chloride and dried over anhydrous MgSO$_4$. The solvent was removed under reduced pressure. To the residue was added toluene (100 ml) followed by addition of 2-(4-nitrobenzyloxycarbonylamino)ethanethiol (2.24 g). Then, K$_2$CO$_3$ (2.90 g, 21.0 mmol) and Aliquat 336 (ca. 0.5 ml) were added with ice-cooling. The mixture was stirred at 4° C. for 64 hours and, then, at room temperature for 1 hour. The precipitate was separated by filtration and washed with toluene. The filtrate and washings were combined and concentrated under reduced pressure. To the residue was added methanol (200 ml) followed by addition of pyridinium p-toluenesulfonate (251 mg, 0.999 mmol). The mixture was stirred at room temperature for 1 hour and, then, concentrated under reduced pressure. The residue was subjected to silica gel column chromatography (70–230 mesh, 200 g; ethyl acetate-hexane =2:3–1:1–3:2-ethyl acetate) to give (3S,4S)-3-[(R)-1-(allyloxycarbonyloxy)ethyl] -4-[(2R)-4-[2-(4-nitrobenzyloxycarbonylamino)ethylthio] -3-oxotetra-hydropyran-2-yl]azetidin-2-one (1.50 g) as a light yellow amorphous solid.

IR (neat): 3325, 1751, 1726. 1520 $^{-1}$. $^1$H-NMR (200 MHz, CDCl$_3$) 5:1.43–1.48 (3H, m), 2.02–2.85 (4H, m), 3.22–4.08 (8H, m), 4.55–4.67 (2H, m), 5.07–5.42 (6H, m), 5.73–6.13 (2H, m), 7.52 (2H, m), 8.22 (2H, m)

Reference Example 37

The compound obtained in Reference Example 36 was reacted as in Reference Example 4 to give allyl [(3S,4S)-3-[(R)-1-(allyloxycarbonyloxy)ethyl]-4-[(2R)-4-[2-(4-nitrobenzyloxycarbonylamino)ethylthio]-3-oxotetrahydropyran-2-yl]-2-oxoazetidin-1-yl]glyoxylate.

IR (neat): 3400, 2950, 1811, 1741, 1724, 1520 $^{-1}$.

Reference Example 38

To a solution of diisopropylamine (2.6 mg) in dry THF (35 ml) was added a solution of n-butyllithium in hexane (10.5 ml) at -78° C. and the mixture was stirred at 0° C. for 30 minutes. The reaction mixture was cooled to −78° C. and a solution of (3S,4S)-3-R-1-[(tert-butyldimethylsilyloxy)ethyl] -4-(3-oxotetrahydropyran-2-yl) -1-(trimethylsilyl)azetidin-2-one (5.58 g) in dry THF (15 ml) was added dropwise over a period of 20 minutes. The mixture was stirred at the same temperature for 30 minutes and, then, a solution of S-methyl benzenethiosulfonate (3.2 g) in dry THF (15 ml) was added dropwise over 10 minutes. The reaction mixture was stirred at the same temperature for 30 minutes and, then, at −30° C. for 10 minutes. The reaction mixture was diluted with a saturated aqueous solution of ammonium chloride (300 ml) and extracted with ether (500 ml). The extract was washed with 1% hydrochloric acid (200 ml), water (200 ml×2) and saturated aqueous sodium chloride solution (200 ml) in the order mentioned. The solvent was then distilled off under reduced pressure and the residue was dissolved in THF-water (9:1, 70 ml) followed by addition of pyridinium p-toluenesulfonate (90 mg). The mixture was then stirred at room temperature for 17 hours. The THF was distilled off under reduced pressure and ether (200 ml) was added to the residue. The mixture was then washed successively with phosphate buffer (pH 7, 100 ml×2) and saturated aqueous sodium chloride solution (100 ml) and dried over anhydrous magnesium sulfate. The solvent was then distilled off under reduced pressure and the residue was subjected to silica gel column chromatography (230–400 mesh, 140 g; ethyl acetate-hexane =1:4) to give 1.73 g of (3S,4S) 3(R)-1-[(tert-butyldimethylsilyloxy)ethyl] -4-[(2R,4S)- 4-methylthio-3-oxotetrahydropyran-2-yl]azetidin-2-one as a light yellow oil.

IR (neat): 2930, 2850, 1760, 1720 $^{-1}$. $^1$H NMR (200 MHz, CDCl$_3$)δ: 0.08 (6H, s), 0.88 (9H, s), 1.25 (3H, d, J=6.4 Hz), 2.06 (3H, s), 2.1–2.7 (2H, m), 3.2–3.3 (1H, m), 3.3–3.4 (1H, m), 3.9–4.2 (3H, m), 4.2–4.3 (1H, m), 4.65 (1H, d, J=3.6 Hz), 5.68 (1H, brs)

Reference Example 39

The compound obtained in Reference Example 38 (1.72 g) was dissolved in dry acetonitrile (10 ml), and with ice-cooling, BF$_3$.OEt$_2$ (0.93 ml) was added. The mixture was stirred at the same temperature for 90 minutes. The reaction mixture was adjusted to pH 7 with a saturated aqueous solution of sodium hydrogen carbonate and after sodium chloride saturation, extracted with ethyl acetate (20 ml×3). The extracts were combined and dried over anhydrous magnesium sulfate. The solvent was then distilled off under reduced pressure and the residue was subjected to silica gel column chromatography (230–400 mesh, 15 g; ethyl acetate) to give 864 mg of (3S,4S)-[(R)-1-hydroxyethyl] -4-[(2R,4S)-4-methylthio-3-oxotetra-hydropyran -2-yl]azetidin-2-one as a light yellow amorphous solid.

IR (KBr): 3450, 2960, 2920, 2850, 1740 cm$^{-1}$.

Reference Example 40

The compound obtained in Reference Example 39 (858 mg) was dissolved in dry THF (15 ml) followed by addition of pyridine (0.7 ml) and allyl chloroformate (0.35 ml, 3.3 mmol) in that order. The mixture was stirred at 30° C. for 1 hour. Then, allyl chloroformate (1.4 ml, 13.2 mmol) was further added in 4 installments over a period of 4 hours. The mixture was stirred at 60° C. for 1 hour, after which it was washed successively with ethyl acetate (100 ml), water (100 ml×2), saturated aqueous solution of copper sulfate (100 ml) and saturated aqueous sodium chloride (100 ml×2) and dried over anhydrous magnesium sulfate. The solvent was then distilled off under reduced pressure and the residue was subjected to silica gel column chromatography (230–400 mesh, 35 g; ethyl acetate-hexane= 1:1) to give (3S,4S)-3-[(R)-1-(allyloxycarbonyloxy)ethyl]   -4-[(2R,4S)-4-methylthio-3 -oxotetrahydropyran-2-yl]azetidin-2-one as a light yellow oil.

IR (neat): 2970, 2910, 2850, 1750 cm$^{-1}$

Reference Example 41

The compound obtained in Reference Example 40 was reacted as in Reference Example 5 to give allyl [(3S,4S)-3-[(R)-1-(allyloxycarbonyloxy)ethyl]-4-[ (2R,4S)-4-methylthio-3-oxotetrahydropyran-2-yl]-2 -oxoazetidin-1-yl]glyoxylate.

IR (neat): 2980, 2920, 1810, 1750, 1700 cm$^{-1}$

Reference Example 42

The compound obtained in Reference Example 23 was reacted as in Reference Example 4 to give allyl [(3S,4S)-3-[(R)-1-(allyloxycarbonyloxy)ethyl]-4-[(2R)- 4-[2-[(tert-butyldimethylsilyloxy)ethyl]-3 -oxotetrahydropyran-2-yl]-2-oxoazetidin-1-yl]glyoxylate.

IR (neat): 2940, 2850, 1810, 1750, 1700 cm$^{-1}$

Reference Example 43

(3S,4S)-4-[(2R)-3-Oxotetrahydropyran-2-yl]-1-(trimethylsilyl) -3-[(R)-1-(trimethylsilyloxy)ethyl] azetidin-2-one was reacted as in Reference Example 38 except that 1,2-bis(allyloxycarbonyl)-4-phenylsulfonylthiopyrazolidine was used in lieu of S-methyl benzenethiosulfonate to give (3S,4S)-4-[(2R)-4-[ [1,2-bis(allyloxycarbonyl)pyrazolidin-4-yl]thio]-3 -oxotetrahydropyran-2-yl]-3-[(R)-1-(trimethylsilyloxy)ethyl] azetidin-2-one.

IR (neat): 2950, 1750, 1710 cm$^{-1}$

Reference Example 44

The compound obtained in Reference Example 43 was reacted as in Reference Example 4 to give allyl (3S,4S)-4-[(2R)-4-[[1,2 -bis(allyloxycarbonyl)pyrazolidin-4-yl]thio]-3 -oxotetrahydropyran-2-yl]-2-oxo-3-[(R)-1-(trimethylsilyloxy)ethyl] azetidin-1-yl]glyoxylate.

IR (neat): 2950, 2930, 1810, 1750, 1700 cm$^{-1}$

Reference Example 45

Sodium (5S, 6R, 7S, 11S)-11-hydroxy-5-[(R)-1-hydroxyethyl ]-4-oxo-3-azatricyclo [5.4.0.0$^{3,6}$]undec-1-ene-2-carboxylate

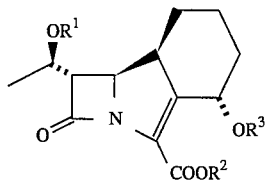

(1) The compound obtained in Reference Example 12 (680 mg) was dissolved in dry xylene (27 ml) followed by addition of triethylphosphite (1.1 ml). The mixture was stirred at 90° C. for 1.5 hours, at 110° C. for 4.5 hours and further at 130° C. for 21 hours. The solvent was then distilled off under reduced pressure and the residue was purified by column chromatography (stationary phase: silica gel 30 g, ethyl acetatehexane 1:19) to give 330 mg of allyl (5S,6R,7S,11S)-5-[ (R)-1-(allyloxycarbonyloxy)ethyl]-4-oxo-11 -trimethylsilyloxy-3-azatricyclo [5.4.0.0$^{3,6}$]undec-1-ene -2-carboxylate (R$^1$=COOCH$_2$CH=CH$_2$, R$^2$=CH$_2$CH=CH$_2$, R$^3$=SiMe$_3$) as a colorless oil.

IR (Neat): 2950, 1780, 1750, 1720, 1640, 1450, 1370 $^{-1}$
$^1$H-NMR (CDCl$_3$)δ: 0.08 (9H, s), 1.19–2.09 (6H, m), 1.45 (3H, d, J=6.3 Hz), 3.35 (1H, dd, J=8.0 & 3.0 Hz), 3.36 (1H, m), 4.13 (1H, dd, J=9.9 & 3.0 Hz), 4.61–4.87 (4H, m), 5.13 (1H, m), 5.24–5.48 (4H, m), 5.85–6.07 (2H, m)

(2) The compound obtained in (1) (35 mg) was dissolved in THF-H$_2$O (2:1, 1 ml), and a solution of pyridinium p-toluenesulfonate (1 mg) in THF-H$_2$O (2:1, 0.5 ml) was added dropwise. The mixture was stirred at room temperature for 2 hours. The reaction mixture was diluted with ethyl acetate, washed successively with water and aqueous sodium chloride solution and dried over anhydrous sodium sulfate. The solvent was then distilled off under reduced pressure and the residue was purified by column chromatography (stationary phase: silica gel 10 g, ethyl acetate-hexane 1:3) to give 28 mg of allyl (5S,6R, 7S,11S)-5-[(R)-1-(allyloxycarbonyloxy)ethyl] -11-hydroxy-4-oxo-3-azatricyclo[ 5.4.0.0$^{3,6}$]undec-1-ene-2-carboxylate (R$^1$=COOCH$_2$CH=CH$_2$, R$^2$=CH$_2$CH=CH$_2$, R$^3$=H) as a colorless oil.

IR (Neat): 3475, 2935, 1775, 1745, 1715, 1445, 1370 cm$^{-1}$ $^1$H-NMR (CDCl$_3$)δ:1.45 (3H, d, J=6.4 Hz), 1.29–2.07 (6H, m), 3.39 (1H, dd, J=7.9 & 3.2 Hz), 3.40 (1H, m), 4.17 (1H, dd, J=10.2 & 3.2 Hz), 4.61–4.86 (4H, m), 5.13 (1H, m), 5.24–5.51 (5H, m), 5.84–6.07 (2H, m)

(3) The compound obtained in (2) (45 mg) and triphenylphosphine (6 mg) were dissolved in dry THF-dichloromethane (1:1, 1.5 ml) followed by addition of a solution of tetrakis(triphenylphosphine)palladium(O) (8 mg), 2-ethylhexanoic acid (17 mg) and sodium 2-ethylhexanoate (19 mg) in dry THF-dichloromethane (1:1, 0.87 ml). The mixture was stirred at room temperature for 1 hour, after which the solvent was distilled off under reduced pressure. To the residue was added ether and the mixture was allowed to stand at −20° C. overnight. The resulting precipitate was recovered by filtration, washed with ether, followed by addition of water (4 ml). The insoluble matter was filtered off and the filtrate was subjected to column chromatography, elution being carried out with water. The eluate was concentrated under reduced pressure and lyophilized to give 26 mg of the title compound (R$^1$=R$^3$=H, R$^2$=Na) as a colorless powder.

IR (KBr): 3450, 1750, 1590, 1400 cm$^{-1}$ $^1$H-NMR (D$_2$O)δ:1.28 (3H, d, J=6.4 Hz), 1.29–2.01 (6H, m), 3.29 (1H, m), 3.42 (1H, dd, J=6.0 & 3.1 Hz), 4.17 (1H, dd, J=10.2 & 3.1 Hz), 4.24 (1H, m), 5.35 (1H, t like, J=2.5 & 2.2 Hz)

Reference Example 46

Sodium (5S,6R,7R,11R)-11-hydroxy-5-[(R)-1-hydroxyethyl] -4-oxo-3-azatricyclo[5.4.0.0$^{3,6}$]undec-1-ene-2 -carboxylate

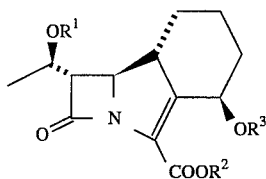

(1) The compound obtained in Reference Example 11 was reacted in the same manner as in Reference Example 45-(1) to give allyl (5S,6R,7R,11R)-5 -[(R)-1 (allyloxycarbonyloxy)ethyl]-4-oxo-11-trimethylsilyloxy- 3-azatricyclo [5.4.0.0$^{3,6}$]undec-1-ene-carboxylate (R$^1$=COOCH$_2$CH=CH$_2$, R$^2$=CH$_2$CH=CH$_2$, R$^3$=SiMe$_3$).

IR (Neat): 2940, 1785, 1745, 1720, 1255 cm$^{-1}$ $^1$H-NMR (CDCl$_3$)δ: 0.09 (9H, s), 1.44 (3H, d, J=6.3 Hz), 1.27–2.21 (6H, m), 3.28 (1H, m), 3.35 (1H, dd, J=7.8 & 3.2 Hz), 3.70 (1H, dd, J=6.8 & 3.2 Hz), 4.61–4.88 (4H, m), 5.11 (1H, m), 5.24–5.48 (5H, m), 5.84–6.08 (2H, m)

(2) The compound obtained in (1) was reacted in the same manner as in Reference Example 45-(2) to give allyl (5S,6R,7R,11R)-5-[(R)-1 (allyloxycarbonyloxy)ethyl]-11-hydroxy-4-oxo-3-azatricyclo[ 5.4.0.0$^{3,6}$]undec-1-ene-2-carboxylate (R$^1$=COOCH$_2$CH=CH$_2$, R$^2$=CH$_2$CH=CH$_2$, R$^3$=H).

IR (Neat): 3500, 2940, 1780, 1745, 1720, 1260 cm$^{-1}$ $^1$H-NMR (CDCl$_3$)δ: 1.45 (3H, d, J=6.4 Hz), 1.29–2.23 (6H, m), 3.28 (1H, m), 3.34 (1H, dd, J=7.7 & 2.9 Hz), 3.76 (1H, dd, J=7.7 & 2.9 Hz), 4.60–4.87 (4H, m), 5.11 (1H, m), 5.25–5.49 (5H, m), 5.84–6.07 (2H, m)

(3) The compound obtained in (2) was reacted in the same manner as in Reference Example 45-(3) to give the title compound (R$^1$=R$^3$=H, R$^2$=Na).

IR (KBr): 3430 2935, 1760, 1595, 1400, 1245 cm$^{-1}$ $^1$H-NMR (D$_2$O)δ: 1.28 (3H, d, J=6.4 Hz), 1.21–2.26 (6H, m), 3.27 (1H, m), 3.42 (1H, dd, J=5.9 & 2.9 Hz), 3.75 (1H, dd, J=7.1 & 2.9 Hz), 4.22 (1H, m), 5.19 (1H, t like, J=2.6 & 2.5 Hz)

EXAMPLE 1

(5S,6R,7S,11R)-5-[(R)-1-Hydroxyethyl]-4-oxo-11-[2-( 1-pyridinio)ethyl]-3-azatricyclo[5.4.0.0$^{3,6}$]undec-1 -ene-2-carboxylate

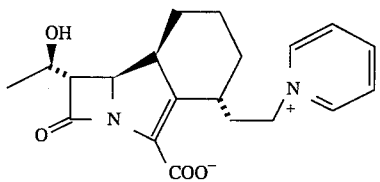

In dichloromethane (4 ml) were dissolved the compound obtained in Reference Example 9 (240 mg) and pyridine (92.5 μl), and a solution of trifluoromethanesulfonic anhydride (96.2 μl) in dichloromethane (2 ml) was added dropwise at 0° C. The mixture was stirred at the same temperature for 2 hours, after which a solution of pyridine (46.2 μl) in dichloromethane (2 ml) was added. The mixture was further stirred at room temperature for 2 hours. The reaction mixture was diluted with toluene (1 ml) and concentrated to dryness under reduced pressure. The residue was dissolved in dichloromethane-THF (1:1, 2 ml) followed by addition of a solution of tetrakis(triphenylphosphine)palladium(O) (165 mg), 2-ethylhexanoic acid (87 mg) and sodium 2-ethylhexanoate (92 mg) in dry THF-dichloromethane (1:1, 4.3 ml). The reaction mixture was stirred at room temperature for 3 hours, at the end of which time the solvent was removed by decantation and the residue was washed with ether. This residue was dissolved in water and the solution was adjusted to pH 7 with aqueous sodium hydrogen carbonate and concentrated under reduced pressure. The residue was subjected to CHP-20 (40 ml) column chromatography, and after the column was rinsed with water, elution was carried out with 10% EtOH. The eluate was concentrated under reduced pressure and lyophilized to give 24 mg of the title compound as a light yellow powder.

IR (KBr): 3440, 2930, 2860, 1750, 1640, 1595 cm$^{-1}$ $^1$H-NMR (D$_2$O)δ:1.2–2.7 (8H, m), 1.26 (3H, d, J=6.4 Hz), 3.0–3.2 (1H, m), 3.33 (1H, dd, J=3.0 & 6.4 Hz), 3.5–3.6 (1H, m), 3.96 (1H, dd, J=3.0 & 10.0 Hz), 4.21 (1H, quintet, J=6.4 Hz), 4.61 (2H, t, J=6.8 Hz), 8.05 (2H, dd, J=5.4 & 8.0 Hz), 8.54 (1H, t, J=8.0 Hz), 8.81 (2H, d, J=5.4 Hz)

EXAMPLE 2

(5S,6R,7R,11S)-5-[(R)-1-Hydroxyethyl]4-oxo-11-[2
-(1-pyridinio)ethyl]-3-azatricyclo[5.4.0.0$^{3,6}$]undec-1 -ene-
2-carboxylate

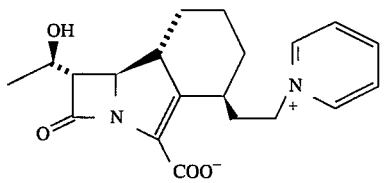

The compound obtained in Reference Example 7 was reacted in the same manner as in Example 1 to give the title compound.

IR (KBr): 3430, 2930, 2860, 1750, 1635, 1590 cm$^{-1}$
$^1$H-NMR (D$_2$O)δ:1.2–2.5 (8H, m), 1.27 (3H, d, J=6.4 Hz), 3.0–3.2 (1H, m), 3.19 (1H, dd, J=2.6 & 6.0 Hz), 3.5–3.6 (1H, m), 3.66 (1H, dd, J=2.6 & 7.0 Hz), 4.20 (1H, dq, J=6.0 & 6.4 Hz), 4.5–4.7 (2H, m), 8.04 (2H, dd, J=5.4 & 7.8 Hz), 8.53 (1H, t, J=7.8 Hz), 8.88 (2H, d, J=5.4 Hz)

EXAMPLE 3

Sodium (5S,6R,7S,11R)-5-[(R)-1-hydroxyethyl]-11-(2-nicotinoyloxyethyl)-4-oxo-3-azatricyclo[5.4.0.0$^{3,6}$] -undec-1-ene-2-carboxylate

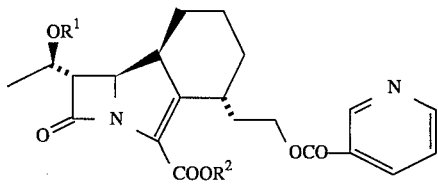

(1) In dichloromethane (8 ml) was suspended nicotinoyl chloride hydrochloride (414 mg) followed by addition of pyridine (0.58 ml). The resulting solution was added dropwise to a solution of the compound obtained in Reference Example 9 (200 mg) in dichloromethane (8 ml) with ice-cooling. The mixture was stirred with ice-cooling for 2 hours, after which it was washed with phosphate buffer (pH 7) and aqueous solution of sodium chloride and dried over anhydrous sodium sulfate. The solvent was distilled off under reduced pressure and the residue was purified by column chromatography (stationary phase: silica gel 20 g, ethyl acetatehexane 1:1) to give 50 mg of allyl (5S,6R,7S,11R)-5-[ (R)-1-(allyloxycarbonyloxy-)ethyl]-11-(2 -nicotinoyloxyethyl)-4-oxo-3-azatricylo [5.4.0.0$^{3,6}$]undec -1-ene-2-carboxylate (R$^1$=COOCH$_2$CH=CH$_2$, R$^2$=CH$_2$CH=CH$_2$) as a colorless oil.

IR (Neat): 2930, 2850, 1775, 1740, 1720 cm$^{-1}$ $^1$H-NMR (CDCl$_2$)δ:1.2–2.2 (8H,m), 1.44 (3H, d, J=6.4 Hz), 3.08 (1H, ddd, J=4.8, 10.2 & 12.8 Hz), 3.35 (1H, dd, J=3.2 & 8.0 Hz), 3.8–4.0 (1H, m), 4.08 (1H, dd, J=3.2 & 10.2 Hz), 4.28 (1H, dt, J=12.0 & 6.7 Hz), 4.36 (1H, dt, J=12.0 & 6.7 Hz), 4.5–4.7 (3H, m), 4.74 (1H, ddt, J=5.4, 13.4 & 1.4 Hz), 5.10 (1H, dq, J=8.0 & 6.4 Hz), 5.22 (1H, dq, J=10.4 & 1.4 Hz), 5.29 (1H, dq, J=10.2 & 1.4 Hz), 5.37 (1H, dq, J=17.2 & 1.4 Hz), 5.38 (1H, dq, J=17.2 & 1.4 Hz), 5.92 (1H, ddt, J=10.2, 17.2 & 5.4 Hz), 5.95 (1H ddt, J=10.4, 17.2 5.4 Hz), 7.41 (1H, ddd, J=0.8, 5.0 & 8.0 Hz), 8.29 (1H, ddd, J=1.8, 2.0 & 8.0 Hz), 8.78 (1H, dd, J=1.8 & 5.0 Hz), 9.22 (1H, dd, J=0.8 & 2.0 Hz)

(2) The compound obtained in (1) (90 mg) and triphenylphosphine (11 mg) were dissolved in dry THF-dichloromethane (1:1, 1.2 ml) followed by addition of a solution of tetrakis(triphenylphosphine)palladium(O) (17 mg), 2-ethylhexanoic acid (19 mg) and sodium 2-ethylhexanoate (22 mg) in dry THF-dichloromethane (1:1, 1.6 ml). The mixture was stirred at room temperature for 24 hours and the solvent was then distilled off under reduced pressure. The residue was diluted with ether and allowed to stand at –20° C. overnight. The resulting precipitate was recovered by filtration and washed with ether. The solid thus obtained was dissolved in water (2 ml) and subjected to CHP-20 (40 ml) column chromatography. The column was washed with water and 5% EtOH, and elution was carried out with 10% EtOH. The eluate was concentrated under reduced pressure and lyophilized to give 50 mg of the title compound (R$^1$=H, R$^2$=Na) as a colorless powder.

IR (KBr): 3430, 2930, 2850, 1750, 1720, 1620, 1490 cm$^{-1}$
$^1$H-NMR (D$_2$O)δ: 1.2–2.4 (8H, m), 1.24 (3H, d, J=6.4 Hz), 3.0–3.2 (1H, m), 3.31 (1H, dd, J=2.8 & 6.4 Hz), 3.6–3.8 (1H, m), 3.86 (1H, dd, J=2.8 & 10.0 Hz), 4.16 (1H, quintet, J=6.4 Hz), 4.3–4.5 (2H, m), 7.62 (1H, dd, J=5.0 & 8.0 Hz), 8.42 (1H, dt, J=8.0 & 1.0 Hz), 8.7–8.8 (1H, m), 9.11 (1H, br.s)

Anal Calcd for C$_{21}$H$_{23}$N$_2$NaO$_6$.2.0H$_2$O: C, 55.02; H, 5.94: N, 6.11
Found: C, 54.90; H, 5.72; N, 5.89

EXAMPLE 4

Sodium (5S,6R,7R,11S)-5-[(R)-1-hydroxyethyl]-11-(2-nicotinoyloxyethyl)-4-oxo-3-azatricyclo[ 5.4.0.0$^{3,6}$]undec-1-ene-2-carboxylate

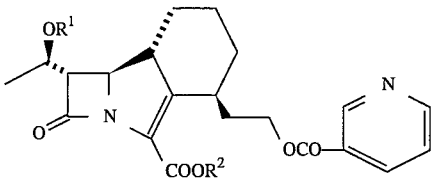

(1) The compound obtained in Reference Example 7 was reacted in the same manner as in Example 3-(1) to give allyl (5S,6R,7R,11S)-5-[(R)-1 -(allyloxycarbonyloxy-)ethyl]-11-(2-nicotinoyloxyethyl) -4-oxo-3-azatricyclo [5.4.0.0$^{3,6}$]-undec-1-ene-2-carboxylate (R$^1$=COOCH$_2$CH=CH$_2$, R$^2$=CH$_2$CH=CH$_2$).

IR (Neat): 2930, 2850, 1780, 1740, 1720 cm$^{-1}$ $^1$H-NMR (CDCl$_3$)δ:1.2–2.2 (8H, m), 1.44 (3H, d, J=6.4 Hz), 3.0–3.2 (1H, m), 3.28 (1H, dd, J=3.0 & 8.0 Hz), 3.6–3.8 (1H, m), 3.73 (1H, dd, J=3.0 & 7.2 Hz), 4.34 (1H, dt, J=12.0 & 6.8 Hz), 4.41 (1H, dt, J=12.0 & 6.8 Hz), 4.63 (2H, dt, J=5.8 & 1.4 Hz), 4.65 (1H, ddt, J=5.4, 13.4 & 1.4 Hz), 4.77 (1H, ddt, J=5.4, 13.4 & 1.4 Hz), 5.10 (1H, dq, J=8.0 & 6.4 Hz), 5.24 (1H, dt, J=10.4 & 1.4 Hz), 5.29 (1H, dt, J=10.2 & 1.4 Hz), 5.36 (1H, dt, J=17.2 & 1.4 Hz), 5.40 (1H, dt, J=17.2 & 1.4 Hz), 5.94 (1H, ddt, J=10.4, 17.2 & 5.4 Hz), 5.95 (1H, ddt, J=10.4, 17.2 & 5.4 Hz), 7.40 (1H, ddd, J=0.8, 4.8 & 8.0 Hz), 8.26 (1H, ddd, J=1.8, 2.0 & 8.0 Hz), 8.78 (1H, dd, J=1.8 & 4.8 Hz), 9.23 (1H, dd, J=0.8 & 2.0 Hz)

(2) The compound obtained in (1) was reacted in the same manner as in Example 3-(2) to give the title compound (R$^1$=H, R$^2$=Na).

IR (Kbr): 3430, 2920, 2850, 1750, 1720 cm$^{-1}$
$^1$H-NMR(D$_2$O)δ:1.19 (3H, d, J=6.4 Hz), 1.2–2.4 (8H, m), 2.97 (1H, dd, J=2.6 & 6.4 Hz), 3.1–3.3 (1H, m), 3.63 (1H, dd, J=2.6 & 7.2 Hz), 3.6–3.7 (1H, m), 4.10 (1H, quintet, J=6.4 Hz), 4.3–4.5 (2H, m), 7.61 (1H, dd, J=5.2 & 8.2 Hz), 8.42 (1H, d, J=8.2 Hz), 8.7–8.8 (1H, m), 9.12 (1H, brs.)

EXAMPLE 5

(5S,6R,7S,11R)-5-[(R)-1-Hydroxyethyl]-11-[2-(1-methyl-1-pyrrolidinio)ethyl]-4-oxo-3-azatricyclo-5.4.0.0$^{3,6}$] undec-1-ene-carboxylate

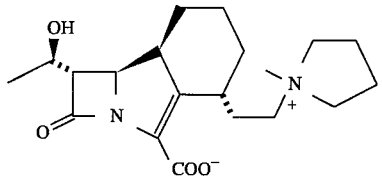

The reaction procedure of Example 1 was repeated using N-methylpyrrolidine in lieu of pyridine to give the title compound.

IR (KBr): 3420, 2930, 2850, 1750, 1620, 1585 cm$^{-1}$
$^1$H-NMR (D$_2$O)δ: 1.28 (3H, d, J=6.4 Hz), 1.2–2.3 (12H, m), 3.05 (3H, s), 3.0–3.3 (2H, m), 3.42 (1H, dd, J=3.0 & 6.0 Hz), 3.4–3.6 (6H, m), 4.15 (1H, dd, J=3.0 & 10.2 Hz), 4.24 (1H, dq, J=6.0 6.4 Hz)

EXAMPLE 6

(5S, 6R, 7R, 11S)-5-[(R)-1-Hydroxyethyl]-11-[2-(1-methyl-1-pyrrolidinio)ethyl]-4-oxo-3-azatricyclo-5.4.0.0$^{3,6}$] undec-1-ene-2-carboxylate

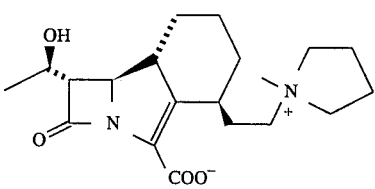

The reaction procedure of Example 5 was repeated to give the title compound.

IR (KBr): 3430, 2920, 2850, 1750, 1620, 1595 cm$^{-1}$
$^1$H-NMR (D$_2$O)δ:1.28 (3H, d, J=6.6 Hz), 1.3–2.3 (12H, m), 3.04 (3H, s), 3.1–3.3 (2H, m), 3.31 (1H, dd, J=2.6 & 6.0 Hz), 3.4–3.6 (6H, m), 3.71 (1H, dd, J=2.6 & 7.4 Hz), 4.22 (1H, dq, J=6.0 & 6.6 Hz)

Anal Calcd for C$_{22}$H$_{30}$N$_2$O$_4$·2.0H$_2$O: C, 60.28; H, 8.60; N, 7.03

Found: C, 60.54; H, 8,84; N, 7.05

EXAMPLE 7

Sodium (5S,6R,7S,11S)-11-carbamoyloxy-5-[(R)-1-hydroxyethyl]-4-oxo-3-azatricyclo[5.4.0.0$^{3,6}$]undec-1-ene-carboxylate

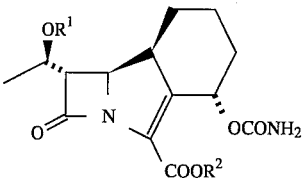

(1) The compound obtained in Reference Example 45-(2) (58 mg) was dissolved in dichloromethane (4 ml) followed by addition of a solution of trichloroacetyl isocyanate (20 μl) in dichloromethane (1 ml) and the mixture was stirred at room temperature for 2 hours. The reaction mixture was concentrated under reduced pressure and the residue was dissolved in methanol (2.5 ml). To this solution was added silica gel (680 mg) and the mixture was stirred at room temperature for 3.5 hours. The silica gel was then filtered off and washed with ethyl acetate. The filtrate and the washes were combined and the solvent was distilled off under reduced pressure. The residue was purified by column chromatography (stationary phase: silica gel 7 g, ethyl acetate-hexane 1:1) to give 43 mg of allyl (5S,6R,7S,11S)-5-[(R)-1-(allyloxycarbonyloxy-)ethyl]-11-carbamoyloxy-4-oxo-3-azatricyclo[5.4.0.0$^{3,6}$] undec-1-ene -2-carboxylate (R$^1$=COOCH$_2$CH=CH$_2$, R$^2$=CH$_2$CH=CH$_2$) as a colorless oil.

IR (Neat): 3490, 3380, 2950, 1780–1710, 1650, 1600 cm$^{-1}$ $^1$H-NMR (CDCl$_3$)δ: 1.45 (3H, d, J=6.4 Hz), 1.25–2.21 (6H, m), 3.35 (1H, ddd, J=12.8, 10.3 & 5.0 Hz), 3.39 (1H, dd, J=8.1 & 3.2 Hz), 4.18 (1H, dd, J=10.3 & 3.2 Hz), 4.61–4.89 (6H, m), 5.11 (1H, m), 5.23–5.47 (4H, m), 5.84–6.07 (2H, m), 6.27 (1H, m)

(2) The compound obtained in (1) (42 mg) and triphenylphosphine (5 mg) were dissolved in THF-dichloromethane (1:1, 1.5 ml) followed by addition of a solution of tetrakis(triphenylphosphine)palladium(O) (6.7 mg), 2-ethylhexanoic acid (14 mg) and sodium 2-ethylhexanoate (16 mg) in dry THF-dichloromethane (1:1, 0.74 ml). The reaction mixture was stirred at room temperature for 1.5 hours, after which the solvent was distilled off under reduced pressure. The residue was diluted with ether and allowed to stand at −20° C. overnight. The precipitate was collected by filtration and washed with ether, followed by addition of water (4 ml). The insoluble matter was filtered off and the filtrate was subjected to CHP-20 (40 ml) column chromatography. Elution was carried out with water and the eluate was concentrated under reduced pressure and lyophilized to give 20 mg of the title compound (R$^1$=H, R$^2$=Na) as a colorless powder.

IR (KBr): 3430, 2930, 1745, 1600, 1400 cm$^{-1}$ $^1$H-NMR (D$_2$O)δ: 1.28 (3H, d, J=6.2 Hz), 1.23–2.50 (6H, m), 3.27 (1H, m), 3.43 (1H, dd, J=6.0 & 3.0 Hz), 4.18 (1H, dd, J=9.9 & 3.0 Hz), 4.21 (1H, m), 6.05 (1H, t like, J=2.9 Hz)

EXAMPLE 8

Sodium (5S,6R,7R,11R)-11-carbamoyloxy-5-[(R)-1-hydroxyethyl]-4-oxo-3-azatricyclo[5.4.0.0³,⁶]undec-1-ene-2-carboxylate

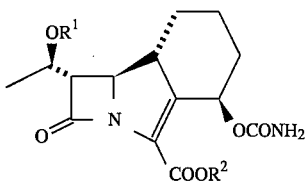

(1) The compound obtained in Reference Example 46-(2) was reacted in the same manner as in example 7-(1) to give allyl (5S,6R,7R,11R)-5-[(R)-(allyloxycarbonyloxy)ethyl]-11-carbamoyloxy-4-oxo-3-azatricyclo [5.4.0.0³,⁶]undec-1-ene-2-carboxylate ($R^1$=COOCH$_2$CH=CH$_2$, $R^2$=CH$_2$CH=CH$_2$).

IR (Neat): 3480, 3370, 2940, 1785, 1740, 1720, 1600, 1450 cm⁻¹ ¹H-NMR (CDCl$_3$)δ:1.45 (3H, d, J=6.4 Hz), 1.28–1.77 (4H, m), 2.12–2.27 (2H, m), 3.38 (1H, dd, J=7.9 & 3.1 Hz), 3.77 (1H, dd, J=7.3 & 3.1 Hz), 4.61–4.79 (6H, m), 5.11 (1H, m), 5.24–5.47 (4H, m), 5.84–6.07 (2H, m), 6.27 (1H, m)

(2) The compound obtained in (1) was reacted in the same manner as in Example 7-(2) to give the title compound ($R^1$=H, $R^2$=Na)

IR (KBr): 3430, 2940, 1750, 1720, 1610, 1400 cm⁻¹ ¹H-NMR (D$_2$O)δ: 1.28 (3H, d, J=6.4 Hz), 1.20–2.82 (6H, m), 3.28 (1H, m), 3.46 (1H, dd, J=5.8 & 3.0 Hz), 3.79 (1H, dd, J=6.9 & 3.0 Hz), 4.20 (1H, m), 5.97 (1H, dd, J=2.3 & 2.6 Hz)

EXAMPLE 9

(10S,11R,12S)-5-Amino-12-[(R)-1-hydroxyethyl]-13-oxo-14-azatetracyclo[8.5.0²,⁷.0¹¹,¹⁴]pentadeca-2,4,6,15(1)-tetraene-15-carboxylic acid

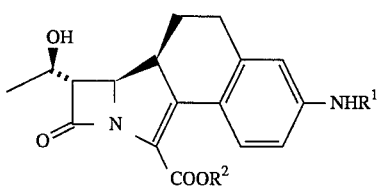

(1) A solution of the compound obtained in Reference Example 16 (5.10 g) in toluene (100 ml) was refluxed for 24 hours and, then, concentrated under reduced pressure. The residue was purified by column chromatography (stationary phase: silica gel 100 g, ethyl acetate-hexane 1:1) to give 413 mg of allyl (10S,11R,12S)-5-allyloxycarbonylamino-12-[(R)-1-hydroxyethyl]-13-oxo-14-azatetracyclo[ 8.5.0²,⁷.0¹¹,¹⁴]pentadeca-2,4,6,15(1)-tetraene-15-carboxylate ($R^1$=COOCH$_2$CH=CH$_2$, $R^2$=CH$_2$CH=CH$_2$) as a light yellow amorphous solid.

IR (KBr): 3435, 3345, 2930, 1765, 1715, 1610, 1580, 1530, 1275, 1220 cm⁻¹ ¹H-NMR (CDCl$_3$)δ: 1.36 (3H, d, J=6.3 Hz), 1.77–2.17 (2H, m), 3.01–3.27 (3H, m), 3.31 (1H, dd, J=6.7 & 3.4 Hz), 4.29 (1H, m), 4.33 (1H, dd, J=10.3 & 3.4 Hz), 4.65–4.91 (4H, m), 5.23–5.47 (4H, m), 5.88–6.11 (2H, m), 6.70 (1H, br.s), 7.04 (1H, dd, J=8.6 & 2.4 Hz), 7.39 (1H, m), 7.82 (1H, d, J=8.6 Hz)

(2) The compound obtained in (1) was reacted in the same manner as in Example 7-(2) to give the title compound ($R^1$=$R^2$=H).

IR (KBr): 3425, 1750, 1610, 1400 cm⁻¹ ¹H-NMR (D$_2$O)δ:1.30 (3H, d, J=6.3 Hz), 1.68–2.21 (2H, m), 2.91–3.02 (2H, m), 3.19 (1H, m), 3.53 (1H, dd, J=5.7 & 1.0 Hz), 4.24–4.37 (2H, m), 6.62–6.67 (2H, m), 7.36 (1H, dd, J=8.7 & 3.5 Hz)

EXAMPLE 10

Sodium (5S,6S,7R)-5-[(R)-1-hydroxyethyl]-4-oxo-8-(propyloxycarbonyl)-3,8-diazatricyclo[5.4.0.0³,⁶]undec-1-ene-2-carboxylate.

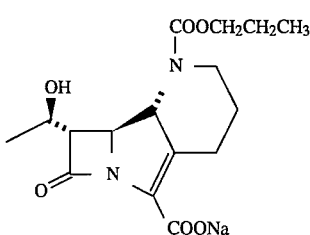

The p-nitrobenzyl (5S,6S,7R)-8-(allyloxycarbonyl)-5-[(R)-1-hydroxyethyl]-4-oxo-3,8-diazatricyclo[ 5.4.0.0³,⁶]undec-1-ene-2-carboxylate (47 mg) was dissolved in tetrahydrofuran-phosphate buffer (pH 7) (2:1, 3 ml), followed by addition of 10% palladium-on-carbon (12 mg). The mixture was stirred in a hydrogen atmosphere at room temperature for 5 hours. The palladium-on-carbon was filtered off through Celite and the filtrate was washed with ethyl acetate. The aqueous layer was purified by CHP-20P column chromatography (eluent: water) to give the title compound (5.4 mg).

IR (KBr): 3430, 2975, 1740, 1600, 1400 cm⁻¹ ¹H-NMR (D$_2$O)δ:0.93 (3H, t, J=7 Hz), 1.32 (3H, d, J=6 Hz), 1.50–2.50 (5H, m), 3.00–3.75 (3H, m), 3.56 (1H, dd, J=5 Hz, 2 Hz), 3.90–4.40 (4H, m), 3.97 (1H, dd, J=8 Hz, 2Hz).

EXAMPLE 11

Allyl (5S,6S,7S,11R)-5-[(R)-1-(allyloxycarbonyloxy)ethyl]-11-(2-hydroxyethyl)-4-oxo-8-oxa-3-azatricyclo[5.4.0.0³,⁶]undec-1-ene-2-carboxylate

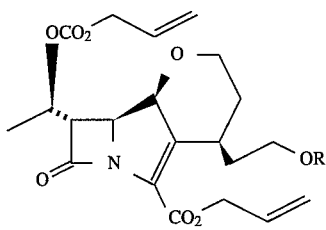

(1) The compound obtained in Reference Example 24 was reacted in the same manner as in Example 9 to give allyl (5S,6S,7S,11S)-5-[(R)-1-(allyloxycarbonyloxy)ethyl]-11-[2-(tert-butyldimethylsilyloxy)ethyl]-4-oxo-8-oxa-3-azatricyclo[ 5.4.0.0³,⁶]undec-1-ene-2-carboxylate [R=$^t$Bu(Me)$_2$].

IR (Neat): 2950, 2920, 2850, 1780, 1740 ⁻¹ ¹H-NMR (CDCl$_3$)δ: 0.02 (6H, s), 0.88 (9H, s), 1.42 (3H, d, J=6.2 Hz), 1.5–2.2 (3H, m), 2.8–3.0 (1H, m), 3.5–3.8 (4H, m), 3.80 (1H, dd, J=3.5 & 6.9 Hz), 4.0–4.2 (1H, m), 4.12 (1H, dd, J=3.5 & 8.0 Hz), 4.30 (1H, d, J=8.0 Hz), 4.62 (2H, dt, J=5.8 1.4 Hz), 4.73 (2H, dt, J=5.8 & 1.4 Hz), 5.16 (1H, dq, J=6.9 & 6.2 Hz), 5.2–5.3 (2H, m), 5.36 (1H, dq, J=17.2 & 1.4 Hz), 5.41 (1H, dq, J=17.2 & 1.4 Hz), 5.8-6.1 (2H, m)

(2) The compound obtained in (1) was reacted in the same manner as in Reference Example 7 to give the title compound (R=H).

IR (Neat): 3530, 2940, 2870, 1785, 1740 cm$^{-1}$ $^1$H-NMR (CDCl$_3$)δ: 1.42 (3H, d, J=6.4 Hz), 1.6–1.9 (3H, m), 2.2–2.4 (1H, m), 2.8–3.0 (1H, m), 3.6–3.8 (4H, m), 3.80 (1H, dd, J=3.4 & 7.0 Hz), 4.0–4.2 (1H, m), 4.12 (1H, dd, J=3.4 & 8.0 Hz), 4.31 (1H, d, J=8 Hz), 4.63 (2H, dt, J=5.6 & 1.2 Hz), 4.75 (2H, dt, J=5.6 & 1.2 Hz), 5.16 (1H, dq, J=7.0 & 6.4 Hz), 5.2–5.3 (2H, m), 5.36 (1H, dq, J=17.2 & 1.2 Hz), 5.43 (1H, dq, J=17.2 & 1.2 Hz), 5.94 (1H, ddt, J=10.4 17.2 & 5.6 Hz), 5.98 (1H, ddt, 10.4, 17.2 & 5.6 Hz)

EXAMPLE 12

Sodium (5S,6S, 7S, 11R)-11-hydroxy-5-[(R)-1-hydroxyethyl] -4-oxo-8-oxa-3-azatricyclo[5.4.0.0$^{3,6}$]undec-1-ene -2-carboxylate

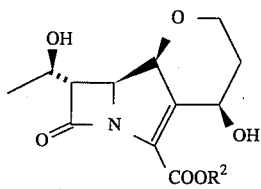

(1) A solution of the compound obtained in Reference Example 29 (220 mg) in toluene (5 ml) was stirred at 50° C. for 4 hours and, then, at 80° C. for 8 hours. The solvent was then distilled off under reduced pressure and the residue was subjected to silica gel column chromatography (70–230 mesh, 20 g; ethyl acetate-hexane =1:2) to give allyl (5S,6S,7S,11R)-11-hydroxy-5-[(R) -1-hydroxyethyl]-4-oxo-8-oxa-3azatricyclo[ 5.4.0.0$^{3,6}$]undec-1-ene-2-carboxylate (R$^2$=CH$_2$CH=CH$_2$) (93 mg).

IR (neat): 3383, 2970, 2929, 2860, 1790, 1693, 630 $^{-1}$. $^1$H-NMR (200 MHz, CDCl$_3$)δ: 1.31 (3H, d, J=6.4Hz), 1.80–1.95 (1H, m), 2.15–2.30 (1H, m), 3.66 (1H, td, J=12.3 Hz and J=12.3 Hz and J=2.4 Hz), 3.66 (1H, dd, J=6.0 Hz and J=3.6 Hz), 4.05–4.20 (1H, m), 4.20 (1H, dd, J=8.6 Hz and 3.6 Hz), 4.37 (1H, d, 8.6 Hz), 4.69–4.93 (3H, m), 5.31 (1H, dq like, J=10.4 Hz and J=1.2 Hz), 5.48 (1H, dq like, J=17.2 Hz and 1.2 Hz), 5.99 (2H, ddt like, J=17.2 Hz, J=10.4 Hz, and J=5.6 Hz), 6.35 (1H, d, J=5.2 Hz)

(2) The compound obtained in (1) was reacted in the same manner as in Reference Example 45 (3 ) to give the title compound (R$^2$=Na).

IR (KBr): 3417, 1765, 1599 cm$^{-1}$ $^1$H-NMR (200 MHz, D$_2$O)δ:1.27 (3H, d, J=6.4 Hz), 1.65–1.90 (1H, m), 2.10–2.25 (1H, m), 3.58 (1H, dd, J=5.4 Hz and J=3.4 Hz), 3.77 (1H, td, J=12.4 Hz and J=2.4 Hz), 4.06–4.20 (1H, m), 4.19 (1H, dd, J=8.2 Hz and 5.4 Hz), 4.57 (1H, d, J=8.2 Hz), 4.70–4.85 (1H, m)

EXAMPLE 13

Allyl (5S,6S,7S,11S)-11-hydroxy-5-[(R)-1-hydroxyethyl] -4-oxo-8-oxa- 3-azatricyclo [5.4.0.0$^{3,6}$]undec-1-ene-2-carboxylate

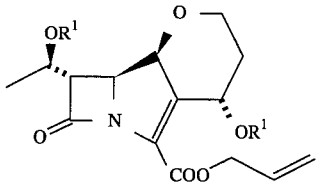

(1) To a solution of the compound obtained in Reference Example 31 (514 mg) in dry THF (2 ml) was added 2,6-lutidine (0.22 ml, 1.89 mmol) and after the solution was cooled to −78° C., thionyl chloride (0.10 ml, 1.35 mmol) was gradually added dropwise. The mixture was stirred at the same temperature for 20 minutes and, then, at 0° C. for 10 minutes. The reaction mixture was concentrated under reduced pressure and toluene was added to the residue. The resulting precipitate was removed by filtration and washed with toluene. The filtrate and washings were combined and concentrated under reduced pressure. The residue was dissolved in THF (5 ml) followed by addition of triphenylphosphine (495 mg, 1.89 mmol) and 2,6-lutidine (0.22 ml, 1.89 mmol) at 0° C. The mixture was stirred at 50° C. for 7 days. The reaction mixture was then concentrated under reduced pressure and the residue was dissolved in ethyl acetate. The solution was washed with water and saturated aqueous solution of copper sulfate and dried over anhydrous magnesium sulfate. Following concentration under reduced pressure, the residue was subjected to silica gel column chromatography (230–400 mesh, 40 g; ethyl acetate-hexane=1:20→1:9) to give allyl (5S,6S,7S,11S)-11 -(tert-butyldimethylsilyloxy)-5-[(R)-1-(tert-butyldimethylsilyloxy)ethyl] -4-oxo-8-oxa-3-azatricyclo[ 5.4.0.0$^{3,6}$]undec-1-ene-2-carboxylate (R$^1$=$^t$BuMe$_2$Si) (80 mg) as a colorless oil.

IR (neat): 2956, 2927, 2885, 2856, 1788, 1755, 1722 cm$^{-1}$. $^1$H-NMR (200 MHz, CDCl$_3$)δ: 0.01 (3H, s), 0.06 (3H, s), 0.08 (3H, s), 0.09 (3H, s), 0.90 (18H, s), 1.19 (3H, d, J=6.2 Hz), 1.63–1.78 (1H, m), 1.83–2.05 (1H, m), 3.58 (1H, dd, J=4.2 Hz and 3.6 Hz), 3.65–3.88 (1H, m), 4.02–4.20 (1H, m), 4.13 (1H, dd, J=8.2 Hz and 3.6 Hz), 4.29 (1H, qd, J=6.2 Hz and 4.2 Hz), 4.70–4.78 (2H, m), 4.82 (1H, d, J=8.2 Hz), 5.22–5.31 (1H, m), 5.37–5.50 (2H, m), 5.96 (1H, ddt, J=17.2 Hz, 10.4 Hz and 5.2 Hz)

(2) The compound obtained in (1) was reacted as in Reference Example 7 to give the title compound (R$^1$=H).

IR (neat): 3365, 2962, 2931, 2878, 1784, 1722 cm$^{-1}$. $^1$H-NMR (200 MHz, CDCl$_3$)δ: 1.32 (3H, d, J=6.4 Hz), 1.80–2.13 (2H, m), 3.69 (1H, dd, J=6.0 Hz and 3.6 Hz), 3.87 (1H, ddd, J=11.4 Hz, 4.6 Hz and 1.5 Hz), 4.14 (1H, td like, J=12.0 Hz and 3.0 Hz), 4.18 (1H, dd, J=8.4 Hz and 3.6 Hz), 4.29 (1H, quintet like, J=6.2 Hz), 4.65–4.90 (1H, m), 4,95 (1H, d, J=8.4 Hz), 5.24–5.51 (2H, m), 5.54 (1H, t, 3.0 Hz)

EXAMPLE 14

(5S,6R,7S,11S)-5-[(R)-1-Hydroxyethyl ]-11-[(1-methyl-1-pyrrolidinio)methyl]-4-oxo-3-azatricyclo[ 5.4.0.0³,⁶]undec-1-ene-2-carboxylate

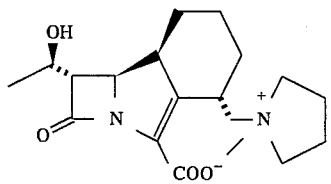

The compound obtained in Reference Example 35 was reacted as in Example 5 to give the title compound.

IR (neat): 3425, 2925, 1750, 1590, 1385 $^{-1}$. $^1$H-NMR (200 MHz, D$_2$O) δ:1.29 (3H, d, J=6.3 Hz) 1.32–2.01 (6H, m) 2.14–2.26 (4H, m) 3.06 (3H, s) 3.20 (1H, m) 3.41 (1H, dd, J=9.8 Hz, J=2.8 Hz) 3.43–3.62 (5H, m) 3.88 (1H, dd, J=13.2 Hz, J=10.3 Hz) 4.16 (1H, dd, J=6.1 Hz, J=2.8 Hz) 4.18–4.31 (2H, m) UV$_{max}$(pH7.1 MOPS buffer) 270 nm

EXAMPLE 15

(5S,6S,7S,11S)-11-[(2-Aminoethyl)thio]-5-[(R)-1-hydroxyethyl] -4-oxo-8-oxa-3-azatricylo [5.4.0.0³,⁶]undec-1-ene-2-carboxylic acid

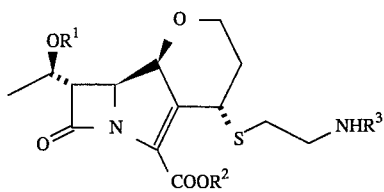

(1) The compound obtained in Reference Example 37 (260 mg) was dissolved in toluene (10 ml) followed by addition of triethyl phosphite (291 mg) and hydroquinone (5 mg) at room temperature. The mixture was stirred in an argon atmosphere at 90° C. for 1 hour. The reaction mixture was then concentrated under reduced pressure and the residue was purified by silica gel column chromatography (230–400 mesh, 20 g; ethyl acetate-hexane= 1:3) and further by preparative TLC (20×20 cm, 2, 0.5 mm, 2 plates; ethyl acetate-hexane=1:1) to give allyl (5S,6S,7S,11S)-5-[(R)-1-(allyloxycarbonyloxy)ethyl] -11-[2-(4-nitrobenzyloxycarbonylamino)ethylthio] -4-oxo-8-oxa-3-azatricyclo[ 5.4.0.0³,⁶]undec-1-ene-2-carboxylate (R$^1$=COOCH$_2$CH=CH$_2$, R$^2$=CH$_2$CH=CH$_2$, R$^3$=COOCH$_2$C$_6$H$_4$NO$_2$) (51 mg) as a colorless oil.

IR (neat): 3392, 2945, 2864, 1792, 1738, 1724, 1520 cm$^{-1}$. $^1$H-NMR (200 MHz, CDCl$_3$)δ: 1.41 (3H, d, J=6.4 Hz) 1.80 (1H, m) 2.26 (1H, m) 2.44–2.69 (2H, m) 3.28–3.50 (2H, m) 3.81 (1H, dd, J=6.4 Hz, J=3.7 Hz) 3.92 (2H, m) 4.22 (1H, dd, J=8.7 Hz, J=3.7 Hz) 4.60–4.92 (6H, m) 5.10–5.53 (8H, m) 5.82–6.10 (2H, m) 7.51 (2H, d, J=8.6 Hz) 8.22 (2H, d, J=8.6 Hz)

(2) In an argon atmosphere, the compound obtained in (1) (55 mg) was dissolved in dry THF-CH$_2$Cl$_2$ (1:1.2 ml) followed by addition of triphenylphosphine (2.5 mg) and Pd (PPh$_3$)$_4$ (5.5 mg). Then, a solution of sodium 2 -ethylhexanoate-2-ethylhexanoic acid in dry THF-CH$_2$Cl$_2$ was added dropwise. The mixture was stirred at room temperature for 30 minutes and, then, concentrated under reduced pressure. To the residue was added ether for solidification. The solid thus obtained was recovered by filtration and washed 3 times with ether. The washed solid was dried in vacuo, and then THF (5 ml) and phosphate buffer (pH 7; 2.5 ml) were added. Following addition of 10% Pd/C (25 mg), the mixture was stirred with ice cooling in a hydrogen atmosphere for 1 hour. This reaction mixture was filtered through Celite and, then, 10% Pd/C (55 mg) was added. The mixture was then stirred in a hydrogen atmosphere with ice-cooling for 1.67 hours. The reaction mixture was filtered through Celite again and 10% Pd/C (55 mg) was added. In a hydrogen atmosphere, the mixture was stirred at room temperature for 2 hours and, then, filtered through Celite. The filtrate was concentrated to about 1 ml under reduced pressure and purified by reversed phase silica gel column chromatography (LiChroprep RP-18, 40–63 µm, 30 ml; elution with water acetonitrile-water 2% acetonitrile) and Sephadex (LH-20, 200 ml; elution with water). The eluate was lyophilized to give the title compound (R$^1$=R$^2$=R$^3$=H) (13 mg) as a colorless powder.

IR (neat): 3442, 1763, 1603, 1165, 1097 cm$^{-1}$. $^1$H-NMR (200 MHz, D$_2$O)δ:1.27 (3H, d, J=6.4 Hz), 1.85 (1H, m), 2.35 (1H, m), 2.75 (2H, m), 3.20 (2H, m), 3.65 (1H, dd, J=4.9 Hz, J=3.7 Hz), 4.01 (2H, m), 4.26 (1H, dd, J=8.8 Hz, J=3.7 Hz), 4.31 (1H, m), 4.88 (1H, m), 5.07 (1H, d, J=8.8 Hz) UV$_{max}$(pH7.1 MOPS buffer) 270 nm

EXAMPLE 16

(5S, 6S, 7S, 11S)-5-[(R)-1-Hydroxyethyl ]-11-[2 -(iminomethylamino)ethylthio]-4-oxo-8-oxa-3-azatricyclo-5.4.0.0³,⁶]undec-1-ene-2-carboxylic acid

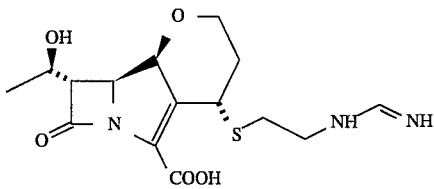

The compound obtained in Example 15 (11 mg) was dissolved in cold water (2 ml) under ice-cooling. This solution was maintained at pH 8–8.5 with 2N K$_2$CO$_3$ and benzyl formamidate hydrochloride (60 mg, 0.350 mmol) was added in several installments. The mixture was stirred at the same temperature for about 20 minutes and, then, adjusted to pH 7 with 1N HCl. The solution was washed with 3 portions of ethyl acetate-THF (9:1) and the aqueous layer was partially concentrated under reduced pressure and purified by reversed phase silica gel column chromatography (LiChroprep RP-18, 40–63 µm, ml; elution with water 1% acetonitrile-water 2% acetonitrile 5% acetonitrile-water) and lyophilizing to give the title compound (9 mg) as a colorless powder.

IR (neat): 3408, 1765, 1718, 1632, 1591, 1394 $^{-1}$. $^1$H-NMR (200 MHz, D$_2$O)δ: 1.27 (3H, d, J=6.4 Hz), 1.84 (1H, m), 2.32 (1H, m), 2.64–2.83 (2H, m), 3.49–3.62 (2H, m), 3.65 (1H, dd, J=4.8 Hz, J=3.6 Hz), 3.94–4.11 (2H, m), 4.25 (1H, dd, J=8.8 Hz, J=3.6 Hz), 4.31 (1H, m), 4.87 (1H, m), 5.05 (1H, d, J=8.8 Hz), 7.82 and 7.84 (1H(2:1),-s) UV$_{max}$ (pH7.1 MOPS buffer) 270 nm

EXAMPLE 17

Sodium (5S,6S,7S,11R)-5-[(R)-1-hydroxyethyl]-11-2-hydroxyethyl)-4-oxo-8-oxa-3-azatricyclo [5.4.0.0$^{3,6}$]undec-1-ene-2-carboxylate

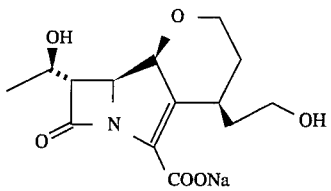

The compound obtained in Example 11 was reacted as in Reference Example 45(3) to give the title compound.

IR (KBr): 3450, 2950, 2850, 1760, 1590 cm$^{-1}$. $^1$H-NMR (200 NMz, D$_2$O)δ:1.27 (3H, d, J=6.4 Hz), 1.4–2.2 (4H, m), 1.7–1.8 (1H, m), 3.60 (1H, dd. J=3.6 and 5.0 Hz), 3.64 (2H, t, J=6.4 Hz), 3.78 (1H, dt, J=2.4 and 12.2 Hz), 4.1–4.2 (1H, m), 4.19 (1H, dd, J=3.6 and 8.0 Hz), 4.29 (1H, dq, J=5.0 and 6.4 Hz), 4.53 (1H, d, J=8.0 Hz)

EXAMPLE 18

Sodium (5S,6S,7S,11S)-5-[(R)-1-hydroxyethyl]-11-methylthio-4-oxo-8-oxa-3-azatricyclo [5.4.0.0$^{3,6}$]undec-1-ene-2-carboxylate

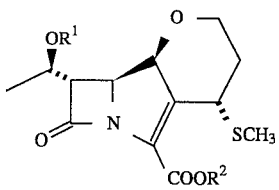

(1) The compound obtained in Reference Example 41 was reacted as in Example 15(1) to give allyl (5S,6S,7S,11S)-5-[(R)-1-(allyloxycarbonyloxy)ethyl]-11-methylthio-4-oxo-8-oxa-3-azatricyclo [5.4.0.0$^{3,6}$]undec-1-ene-2-carboxylate (R$^1$=COOCH$_2$CH=CH$_2$, R$^2$=CH$_2$CH=CH$_2$).

IR (neat): 2980, 2960, 1790, 1740, 1720 cm$^{-1}$. $^1$H NMR (200 MHz, CDCl$_3$)δ:1.42 (3H, d, J=6.2 Hz), 1.8–1.9 (1H, m), 2.02 (3H, s), 2.1–2.4 (1H, m), 3.82 (1H, dd, J=3.8 and 6.6 Hz), 3.8–4.1 (2H, m), 4.22 (1H, dd, J=3.8 and 8.6 Hz), 4.63 (2H, dt, J=5.8 and 1.4 Hz), 4.76 (2H, ddt, J=5.8, 13.4 and 1.4 Hz), 4.77 (1H, dd, J=1.8 and 5.6 Hz), 4.92 (1H, d, J=8.6 Hz), 5.18 (1H, dq, J=6.6 and 6.2 Hz), 5.2–5.5 (4H, m), 5.94 (1H, ddt, J=10.4, 17.2 and 5.8 Hz), 5.97 (1H, ddt, J=10.4, 17.2, and 5.8 Hz)

(2) The compound obtained in (1) was reacted as in Reference Example 45(3) to give the title compound (R$^1$=H, R$^2$=Na).

IR (KBr): 3450, 2960, 2910, 2850, 1760, 1600 cm$^{-1}$. $^1$H NMR (200 MHz, D$_2$O) δ:1.27 (3H, d, J=6.2 Hz), 1.8–1.9 (1H, m), 2.02 (3H, s), 2.2–2.4 (1H, m), 3.64 (1H, dd, J=3.6 and 4.8 Hz), 3.9–4.1 (2H, m), 4.25 (1H, dd, J=3.6 and 8.6 Hz), 4.30 (1H, dq, J=4.8 and 6.2 Hz), 4.67 (1H, dd, J=1.2 and 5.2 Hz), 5.03 (1H, d, J=8.6 Hz)

EXAMPLE 19

Sodium (5S, 6S, 7S, 11S)-5-[(R)-1-hydroxyethyl]-11-2-hydroxyethyl)-4-oxo-8-oxa-3-azatricyclo [5.4.0.0$^{3,6}$]undec-1-ene-2-carboxylate

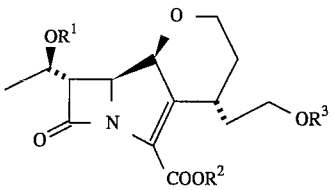

(1) The compound obtained in Reference Example 42 was reacted as in Reference Example 6 to give allyl (5S,6S,7S,11R)-5-[(R)-1-(allyloxycarbonyloxy)ethyl]-11-[2-(tert-butyldimethylsilyloxy)ethyl]-4-oxo-8-oxa-3-azatricyclo[ 5.4.0.0$^{3,6}$]undec-1-ene-2-carboxylate (R$^1$=COOCH$_2$CH=CH$_2$, R$^2$=CH$_2$CH=CH$_2$, R$^3$=$^t$BuMe$_2$Si).

IR (neat): 2940, 2860, 1790, 1750, 1720 cm$^1$. $^1$H NMR (200 MHz, CDCl$_3$)δ: 0.02 (6H, s), 0.87 (9H, s), 1.42 (3H, d, J=6.4 Hz), 1.6–2.1 (4H, m), 3.5–3.9 (5H, m), 3.78 (1H, dd, J=3.6 and 6.8 Hz), 4.11 (1H, dd, J=3.6 and 8.4 Hz), 4.62 (1H, d, J=8.4 Hz), 4.63 (2H, dt, J=5.6 and 1.4 Hz), 4.6–4.9 (2H, m), 5.18 (1H, dq, J=6.8 and 6.4 Hz), 5.2–5.5 (4H, m), 5.8–6.1 (2H, m)

(2) The compound obtained in (1) was reacted as in Reference Example 7 to give allyl (5S,6S,7S,11R)-5-[ (R)-1-(allyloxycarbonyloxy)ethyl]-11-(2-hydroxyethyl]- 4-oxo-8-oxa-3-azatricyclo[5.4.0.0$^{3,6}$]undec-1-ene-2-carboxylate (R$^1$=COOCH$_2$CH=CH$_2$, R$^2$=CH$_2$CH=CH$_2$, R$^3$=H).

IR (neat): 3500, 2950, 1790, 1750, 1720$^{-1}$. $^1$H NMR (200 MHz, CDCl$_3$)δ:1.42 (3H, d, J=6.5 Hz), 1.5–2.2 (4H, m), 2.7–2.8 (1H, m), 3.41–4.0 (5H, m), 3.82 (1H, dd, J=3.6 and 6.5 Hz), 4.17 (1H, dd, J=3.6 and 8.5 Hz), 4.55 (1H, d, J=8.5 Hz), 4.63 (2H, dt. J=5.8 and 1.2 Hz), 4.7–4.9 (2H, m), 5.18 (1H, quintet, J=6.5 Hz), 5.3–5.6 (4H, m), 5.8–6.1 (2H, m)

(3) The compound obtained in (2) was reacted as in Reference Example 45(3) to give the title compound (R$^1$=R$^3$=H, R$^2$=Na).

IR (KBr): 3400, 2940, 2870, 1770, 1600$^{-1}$. $^1$H NMR (200 MHz, D$_2$O)δ:1.27 (3H, d, J=6.4 Hz), 1.6–2.2 (4H, m), 3.5–3.6 (4H, m), 3.9–4.0 (2H, m), 4.16 (1H, dd, J=3.4 and 8.4 Hz), 4.29 (1H, dq, J=5.0 and 6.4 Hz), 4.81 (1H, d, J=8.4 Hz)

EXAMPLE 20

(5S, 6S, 7S, 11S)-5-[(R)-1-Hydroxyethyl]-11-[2-(1-methyl-1-pyrrolidinio)ethyl]-4-oxo-8-oxa-3-azatricyclo-[ 5.4.0.0$^{3,6}$]undec-1-ene-2-carboxylate

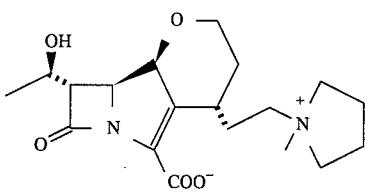

The compound obtained in Example 19(2) was reacted as in Example 5 to give the title compound.

IR (KBr): 3400, 2970, 1765, 1600$^{-1}$. $^1$H NMR (200

MHz, D₂O)δ: 1.27 (3H, d, J=6.2 Hz), 1.7–1.8 (1H, m), 2.0–2.4 (7H, m), 3.06 (3H, s), 3.1–3.6 (7H, m), 3.61 (1H, dd, J=3.6 and 5.0 Hz), 3.9–4.0 (2H, m), 4.19 (1H, dd, J=3.6 and 8.6 Hz), 4.30 (1H, dq, J=5.0 and 6.4 Hz), 4.85 (1H, d, J=8.6 Hz)

EXAMPLE 21

(5S,6S,7S,11S)-5-[(R)-1-Hydroxyethyl]-4-oxo-11-[2-(1-pyridinio)ethyl]-8-oxa-3azatricyclo [5.4.0.0³,⁶]undec-1-ene-2-carboxylate

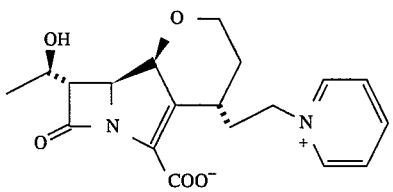

The compound obtained in Example 19(2) was reacted as in Example 1 to give the title compound.

IR (KBr): 3450, 2970, 2820, 1760, 1600 cm⁻¹. ¹H NMR (200 MHz, D₂O)δ: 1.26 (3H, d, J=6.6 Hz), 1.6–2.8 (4H, m), 3.5–3.7 (1H, m), 3.54 (1H, dd, J=3.6 and 5.0 Hz), 3.9–4.0 (2H, m), 4.06 (1H, dd, J=3.6 and 8.0 Hz), 4.29 (1H, dq, J=5.0 and 6.6 Hz), 4.6–4.7 (2H, m), 4.82 (1H, d, J=8.0 Hz), 8.06 (2H, dd, J=6.4 and 7.6 Hz), 8.56 (1H, dt, J=1.2 and 7.6 Hz), 8.84 (2H, dd, J=1.2 and 6.4 Hz)

EXAMPLE 22

(5S,6S,7S,11S)-5-[(R)-1-Hydroxyethyl]-11-[2-(3-methyl-1-imidazolio)ethyl]-4-oxo-8-oxa-3-azatricyclo-[5.4.0.0³,⁶]undec-1-ene-2-carboxylate

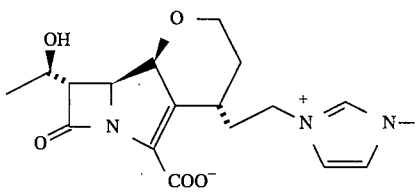

The compound obtained in Example 19(2) was reacted as in Example 1 except that N-methylimidazole was used in lieu of pyridine to give the title compound.

IR (KBr): 3450, 2950, 2860, 1760, 1590 cm⁻¹. ¹H NMR (200 MHz, D₂O)δ: 1.26 (3H, d, J=6.4 Hz), 1.7–2.7 (4H, m), 3.5–3.6 (1H, m), 3.54 (1H, dd, J=3.4 and 5.0 Hz), 3.88 (3H, s), 3.9–4.0 (2H, m), 4.09 (1H, dd, J=3.4 and 8.2 Hz), 4.2–4.3 (2H, m), 4.29 (1H, dq, J=5.0 and 6.2 Hz), 4.81 (1H, d, J=8.2 Hz), 7.44 (1H, s), 7.51 (1H, s), 8.59 (1H, s)

EXAMPLE 23

(5S,6S,7S,11S)-5-[(R)-1-Hydroxyethyl]-4-oxo-11-[2-(1-pyrrolidinyl)ethyl]-8-oxa-3-azatricyclo[5.4.0.0³,⁶]-undec-1-ene-2-carboxylic acid

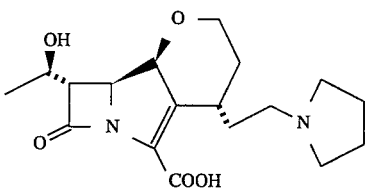

The compound obtained in Example 19(2) was reacted as in Example 1 except that pyrrolidine was used in lieu of pyridine to give the title compound.

IR (KBr): 3400, 2950, 2860, 1760, 1590⁻¹. ¹H NMR (200 MHz, D₂O)δ: 1.27 (3H, d, J=6.2 Hz), 1.6–2.4 (8H, m), 2.9–3.8 (7H, m), 3.60 (1H, dd, J=3.6 and 5.0 Hz), 3.9–4.0 (2H, m), 4.19 (1H, dd, J=3.6 and 8.0 Hz), 4.31 (1H, dq, J=5.0 and 6.2 Hz)

Example 24

(5S,6S,7S)-5-[(R)-1-Hydroxyethyl]-4-oxo-11-[(pyrazolidin-4-yl)thio]-8-oxa-3-azatricyclo[5.4.0.0³,⁶]undec-1-ene-2-carboxylic acid

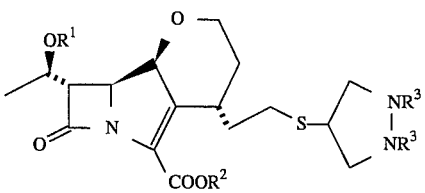

(1) The compound obtained in Reference Example 44 was reacted as in Example 15(1) to give allyl (5S,6S,7S)-11-[[1,2-bis(allyloxycarbonyl)pyrazolidin-4-yl]thio]-4-oxo-5-[(R)-1-(trimethylsilyloxy)ethyl]-8-oxa-3-azatricyclo[ 5.4.0.0³,⁶]undec-1-ene-2-carboxylate (R¹=Me₃Si, R²=CH₂CH=CH₂, R³=COOCH₂CH=CH₂).

IR (neat): 2950, 1790, 1710 cm⁻¹. ¹H-NM(CDCl₃)δ: 0.14 (9H, s), 1.20 (3H, d, J=6.2 Hz), 1.7–1.9 (1H, m), 2.2–2.4 (1H, m), 3.1–3.5 (3H, m), 3.62 (1H, dd, J=3.6 and 4.8 Hz), 3.8–3.9 (2H, m), 4.1–4.3 (1H, m), 4.24 (1H, dd, J=3.6 and 9.0 Hz), 4.28 (1H, dq, J=4.8 and 6.2 Hz), 4.6–5.0 (8H, m), 5.2–5.5 (6H, m), 5.8–6.1 (3H, m)

(2) The compound obtained in (1) (395 mg) was dissolved in THF-water (2:1, 6 ml) and, then, a solution of pyridinium p-toluenesulfonate (1.5 mg) in THF-water (2:1, 1 ml) was added dropwise. The mixture was stirred at room temperature for 30 minutes. The reaction mixture was diluted with ethyl acetate, washed with water and saturated aqueous sodium chloride solution in that order and dried. The solvent was distilled off under reduced pressure and the residue was purified by silica gel column chromatography (silica gel 10 g; ethyl acetate-hexane 3:2) to give allyl (5S,6S,7S)-11-[[1,2-bis(allyloxycarbonyl)pyrazolidin-4-yl]thio]-5-[(R)-1-hydroxyethyl]-4-oxo-8-oxa-3-azatricyclo[5.4.0.0³,⁶]undec-1-ene-2-carboxylate (R¹=H, R²=CH₂CH=CH₂, R³=COOCH₂CH=CH₂).

IR (KBr): 3450, 2950, 1780, 1710⁻¹. ¹H-NMR (CDCl₃)δ: 1.32 (3H, d, J=6.4 Hz), 1.74 (1H, d, J=5.0 Hz), 1.8–1.9 (1H, m), 2.2–2.4 (1H, m), 3.1–3.5 (3H, m), 3.68 (1H, dd, J=3.8 and 5.6 Hz), 3.9–4.0 (2H, m), 4.1–4.2 (1H, m), 4.25 (1H, dd, J=3.8 and 8.4 Hz), 4.2–4.4 (1H, m), 4.6

5.0 (8H, m), 5.2–5.5 (6H, m), 5.8–6.1 (3H, m)

(3) The compound obtained in (2) (27 mg) was dissolved in dry dichloromethane (1 ml). Then, under ice-cooling, dimethylaminotrimethylsilane (46 μl) and tetrakis(triphenylphosphine)palladium(O) (2.8 mg) were added and the mixture was stirred at the same temperature for 1 hour. The reaction mixture was diluted with acetic acid (17 μl) and water (15 ml), and washed with ether. The mixture was then concentrated under reduced pressure and the residue was purified by Diaion CHP20P column chromatography and Sephadex LH-20 column chromatography, and finally lyophilized to give 7 mg of the title compound ($R^1=R^2=R^3=H$) as a colorless powder.

IR (KBr): 3420, 2960, 1770, 1600 cm$^{-1}$. $^1$H-NMR ($D_2O$)δ: 1.25 (3H, d, J=6.4 Hz), 1.7–1.9 (1H, m), 2.2–2.4 (1H, m), 3.1–3.4 (1H, m), 3.5–3.8 (2H, m), 3.63 (1H, dd, J=3.6 and 4.6 Hz), 3.9–4.0 (2H, m), 4.26 (1H, dd, J=3.6 and 8.2 Hz), 4.29 (1H, dq, J=4.6 and 6.4 Hz)

EXAMPLE 25

(5S, 6S,7S,11R)-5-[(R)-1-Hydroxyethyl]-11 [2-(1-methyl-1-pyrrolidinio)ethyl]-4-oxo-8-oxa-3-azatricyclo[5.4.0.0$^{3,6}$]undec-1-ene-2-carboxylate

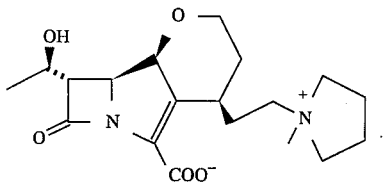

The compound obtained in Example 11(2) was reacted as in Example 5 to give the title compound.

IR (KBr): 3400, 2960, 1760, 1590 cm$^{-1}$. $^1$H-NMR ($D_2O$)δ: 1.27 (3H, d, J=6.2 Hz), 1.6–2.5 (8H, m), 2.6–2.8 (1H, m), 3.05 (3H, s), 3.3–3.5 (8H, m), 3.62 (1H, dd, J=3.6 and 4.8 Hz), 3.7–3.9 (1H, m), 4.1–4.2 (1H, m), 4.19 (1H, dd, J=3.6 and 8.0 Hz), 4.29 (1H, aq, J=4.8 and 6.2 Hz), 4.53 (1H, d, J=8.0 Hz)

What we claimed is:

1. A tricyclic carbapenem compound of the formula:

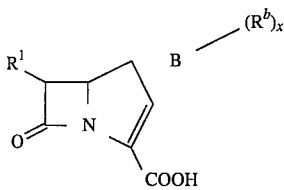

wherein $R^1$ is hydrogen, a substituted or unsubstituted lower alkyl, lower alkenyl, lower alkynyl or cycloalkyl group, wherein said substitution is by 1 to 3 substituent groups, which are the same or different and are selected from the group consisting of cyano, amino, hydroxy, halogen, sulfamoyl, sulfoxy, mono-($C_1$–$C_4$) alkylamino, di-($C_1$–$C_4$) alkylamino, ($C_1$–$C_4$) alkyloxy, carbamoyloxy, ($C_1$–$C_4$) alkylthio, ($C_1$–$C_4$) alkylsulfonyl, and ($C_1$–$C_4$) alkoxycarbonyl; ring B is a saturated or unsaturated six-membered heterocycle containing 1 to 2 hetero-atoms selected from the group consisting of sulfur and oxygen;

x is 1 to 3;

$R^b$ is selected from an alkyloxycarbonyl group or a group of the formula —($W^b$)$_y$—$U^b$ where y is 0 or 1, $W^b$ is selected from —S—,

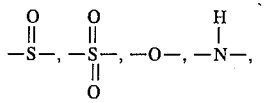

straight or branched-chain lower alkylene or alkenylene groups wherein said alkylene and alkenylene groups uninterrupted or interrupted by a sulfur linkage, a sulfur monooxide linkage, a sulfur dioxide linkage, an oxygen linkage or a substituted or unsubstituted NH linkage wherein the substituent is selected from the group consisting of ($C_1$–$C_6$) alkyl, ($C_2$–$C_6$) alkenyl, ($C_6$–$C_{10}$) aryl, ($C_7$–$C_{12}$) aralkyl, ($C_3$–$C_6$) cycloalkyl, azetidine, furan, pyrrole, pyrrolidine, thiophene, tetrahydrothiophene, thiazole, isothiazole, thiazoline, thiazolidine, oxazole, isoxazole, oxazoline, oxazolidine, pyrazole, pyrazoline, imidazole, imidazoline, thiadiazole, triazole, tetrazole, pyridine, pyrimidine, pyridazine, triazine, morpholine, piperazine, piperidine, quinuclidine, cyano, amino, mono-($C_1$–$C_4$) alkylamino, di-($C_1$–$C_4$) alkylamino, acylamino, hydroxy, ($C_1$–$C_4$) alkyloxy, acyloxy, carbamoyloxy, mono-($C_1$–$C_4$) alkylcarbamoyloxy, di-($C_1$–$C_4$) alkylcarbamoyloxy, ($C_1$–$C_4$) alkylthio, ($C_1$–$C_4$) alkylsulfinyl, ($C_1$–$C_4$) alkylsulfonyl, ($C_1$–$C_4$) alkylsulfonylamino, halogen, sulfamoyl, mono-($C_1$–$C_4$) alkylsulfamoyl, di-($C_1$–$C_4$)-alkylsulfamoyl, ($C_1$–$C_4$) alkoxycarbonyl, carboxy, carbamoyl, mono-($C_1$–$C_4$) alkylcarbamoyl, and di-($C_1$–$C_4$) alkylcarbamoyl groups;

$U^b$ is a) a cyano, amino, carbamoyl, carboxy, sulfamoyl, halogen, amidino, hydroxy, or methyl group, b) an unsubstituted or substituted aromatic hydrocarbon, heterocyclic, c) an unsubstituted or substituted alkylamino, alkylammonium, acylamino, alkyloxy, alkylthio, alkylsulfonyl, alkylsulfonylamino, acyloxy or alkylcarbamoyl or d) a group of the formula

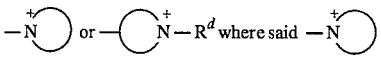

is unsubstituted or substituted pyridinium, pyridazinium, pyrimidinium, pyrazinium, pyrazolium, triazolium, imidazolium, thiazolium, oxazolium, thiadiazolium, isothiazolium, isoxazolium, N-methylpyrrolidinium, quinolinium, isoquinolinium, quinoxalinium, isocinnolinium, thienopyridinium, imidazolopyridinium, imidazolopyridazinium, triazolopyridinium, triazolopyridazinium, triazolopyridazinium, quinuclidinium or dihydropyrazolotriazolium; and $R^d$ is an unsubstituted or substituted alkyl group wherein the substituent which is substituted in the b) groups, c) groups and d) groups above is selected from the group consisting of ($C_1$–$C_6$) alkyl, ($C_2$–$C_6$) alkenyl, ($C_6$–$C_{10}$) aryl, ($C_7$–$C_{12}$) aralkyl, ($C_3$–$C_6$) cycloalkyl, azetidine, furan, pyrrole, pyrrolidine, thiophene, tetrahydrothiophene, thiazole, isothiazole, thiazoline, thiazolidine, oxazole, isoxazole, oxazoline, oxazolidine, pyrazole, pyrazoline, imidazole, imidazoline, thiadiazole, triazole, tetrazole, pyridine, pyrimidine, pyridazine, triazine, morpholine, piperazine, piperidine, quinuclidine, cyano, amino, mono-($C_1$–$C_4$) alkylamino, di-($C_1$–$C_4$) alkylamino, acylamino, hydroxyl, ($C_1$–$C_4$) alkyloxy, acyloxy, carbamoyloxy, mono-($C_1$–$C_4$)

alkylcarbamoyloxy, di-($C_1$–$C_4$) alkylcarbamoyloxy, ($C_1$–$C_4$) alkylthio, ($C_1$–$C_4$)-alkylsulfinyl, ($C_1$–$C_4$) alkylsulfonyl, ($C_1$–$C_4$) alkylsulfonylamino, halogen, sulfamoyl, mono-($C_1$–$C_4$) alkylsulfamoyl, di-($C_1$–$C_4$) alkylsulfamoyl, ($C_1$–$C_4$)-alkoxycarbonyl, carboxy, carbamoyl, mono-($C_1$–$C_4$) alkylcarbamoyl and di-($C_1$–$C_4$) alkylcarbamoyl groups; or pharmaceutically acceptable salts or esters thereof.

2. A tetracyclic carbapenem compound of the formula:

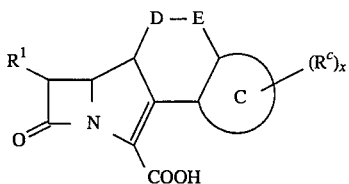

wherein $R^1$ is hydrogen, a substituted or unsubstituted lower alkyl, lower alkenyl, lower alkynyl or cycloalkyl group, wherein said substitution is by 1 to 3 substituent groups, which are the same or different and are selected from the group consisting of cyano, amino, hydroxy, halogen, sulfamoyl, sulfoxy, mono-($C_1$–$C_4$) alkylamino, di-($C_1$–$C_4$) alkylamino, ($C_1$–$C_4$) alkyloxy, carbamoyloxy, ($C_1$–$C_4$) alkylthio, ($C_1$–$C_4$) alkylsulfonyl, and ($C_1$–$C_4$) alkoxycarbonyl; D and E each is selected from the group consisting of $CH_2$, O, S and NH;

ring C is a benzene ring or a 5- or 6-membered aromatic heterocycle containing 1 to 3 hetero-atoms selected from nitrogen, oxygen and sulfur atoms;

x is 1 to 3;

$R^c$ is 1) an unsubstituted or substituted alkylammoniumalkyloxy, alkylaminoalkyloxy, or alkylsulfonylaminoalkyloxy group, wherein said substituent is selected from the group consisting of ($C_1$–$C_6$) alkyl, ($C_2$–$C_6$) alkenyl, ($C_6$–$C_{10}$) aryl, ($C_7$–$C_{12}$) aralkyl, ($C_3$–$C_6$) cycloalkyl, azetidine, furan, pyrrole, pyrrolidine, thiophene, tetrahydrothiophene, thiazole, isothiazole, thiazoline, thiazolidine, oxazole, isoxazole, oxazoline, oxazolidine, pyrazole, pyrazoline, imidazole, imidazoline, thiadiazole, triazole, tetrazole, pyridine, pyrimidine, pyridazine, triazine, morpholine, piperazine, piperidine, quinuclidine, cyano, amino, mono-($C_1$–$C_4$) alkylamino, di-($C_1$–$C_4$) alkylamino, acylamino, hydroxyl, ($C_1$–$C_4$) alkyloxy, acyloxy, carbamoyloxy, mono-($C_1$–$C_4$) alkylcarbamoyloxy, di-($C_1$–$C_4$) alkylcarbamoyloxy, ($C_1$–$C_4$) alkylthio, ($C_1$–$C_4$)-alkylsulfinyl, ($C_1$–$C_4$) alkylsulfonyl, ($C_1$–$C_4$)alkylsulfonylamino, halogen, sulfamoyl, mono-($C_1$–$C_4$) alkylsulfamoyl, di-($C_1$–$C_4$) alkylsulfamoyl, ($C_1$–$C_4$)-alkoxycarbonyl, carboxy, carbamoyl, mono-($C_1$–$C_4$) alkylcarbamoyl and di-($C_1$–$C_4$) alkylcarbamoyl groups, 2) a group of the formula —($W^c$)$_y$—$U^c$, where y is 0 or 1, $W^c$ is selected from —S—,

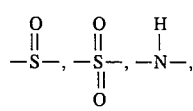

straight or branched-chain lower alkylene or alkenylene groups wherein said alkylene and alkenylene groups uninterrupted or interrupted by a sulfur linkage, a sulfur monooxide linkage, a sulfur dioxide linkage, or a substituted or unsubstituted NH linkage wherein the substituent is selected from the group consisting of ($C_1$–$C_6$) alkyl, ($C_2$–$C_6$) alkenyl, ($C_6$–$C_{10}$) aryl, ($C_7$–$C_{12}$) aralkyl, ($C_3$–$C_6$) cycloalkyl, azetidine, furan, pyrrole, pyrrolidine, thiophene, tetrahydrothiophene, thiazole, isothiazole, thiazoline, thiazolidine, oxazole, isoxazole, oxazoline, oxazolidine, pyrazole, pyrazoline, imidazole, imidazoline, thiadiazole, triazole, tetrazole, pyridine, pyrimidine, pyridazine, triazine, morpholine, piperazine, piperidine, quinuclidine, cyano, amino, mono-($C_1$–$C_4$) alkylamino, di-($C_1$–$C_4$) alkylamino, acylamino, hydroxy, ($C_1$–$C_4$)alkyloxy, acyloxy, carbamoyloxy, mono-($C_1$–$C_4$) alkylcarbamoyloxy, di-($C_1$–$C_4$)-alkylcarbamoyloxy, ($C_1$–$C_4$) alkylthio, ($C_1$–$C_4$) alkylsulfinyl, ($C_1$–$C_4$) alkylsulfonyl, ($C_1$–$C_4$) alkylsulfonylamino, halogen, sulfamoyl, mono-($C_1$–$C_4$) alkylsulfamoyl, di-($C_1$–$C_4$)-alkylsulfamoyl, ($C_1$–$C_4$) alkoxycarbonyl, carboxy, carbamoyl, mono-($C_1$–$C_4$) alkylcarbamoyl, and di-($C_1$–$C_4$) alkylcarbamoyl groups;

$U^c$ is a) a cyano, amino, carbamoyl, carboxy, sulfamoyl, halogen, amidino, hydroxy, or methyl group, b) an unsubstituted or substituted aromatic hydrocarbon, heterocyclic, alkylamino, alkylammonium, acylamino, alkyloxy, alkylthio, alkylsulfonyl, alkylsulfonylamino, acyloxy or alkylcarbamoyl group or c) a group of the formula

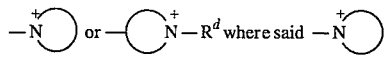

is unsubstituted or substituted pyridinium, pyridazinium., pyrimidinium, pyrazinium, pyrazolium, triazolium, imidazolium, thiazolium., oxazolium, thiadiazolium, isothiazolium, isoxazolium, N-methylpyrrolidinium, quinolinium, isoquinolinium, quinoxalinium, isocinnolinium, thienopyridinium, imidazolopyridinium, imidazolopyridazinium, triazolopyridinium, triazolopyridazinium, triazolopyridazinium, quinuclidinium or dihydropyrazolotriazolium;

$R^d$ is an unsubstituted or substituted alkyl group and wherein the substituent which is substituted in the b) and c) groups above is selected from the group consisting of ($C_1$–$C_6$) alkyl, ($C_2$–$C_6$) alkenyl, ($C_6$–$C_{10}$) aryl, ($C_7$–$C_{12}$) aralkyl, ($C_3$–C6) cycloalkyl, azetidine, furan, pyrrole, pyrrolidine, thiophene, tetrahydrothiophene, thiazole, isothiazole, thiazoline, thiazolidine, oxazole, isoxazole, oxazoline, oxazolidine, pyrazole, pyrazoline, imidazole, imidazoline, thiadiazole, triazole, tetrazole, pyridine, pyrimidine, pyridazine, triazine, morpholine, piperazine, piperidine, quinuclidine, cyano, amino, mono-($C_1C_4$) alkylamino, di-($C_1C_4$) alkylamino, acylamino, hydroxyl, ($C_1$–$C_4$) alkyloxy, acyloxy, carbamoyloxy, mono-($C_1C_4$) alkylcarbamoyloxy, di-($C_1$–$C_4$) alkylcarbamoyloxy, ($C_1$–$C_4$) alkylthio, ($C_1$–$C_4$)-alkylsulfinyl, ($C_1$–$C_4$) alkylsulfonyl, ($C_1$–$C_4$)-alkylsulfonylamino, halogen, sulfamoyl, mono-($C_1$–$C_4$) alkylsulfamoyl, di-($C_{C4}$) alkylsulfamoyl, ($C_1$–$C_4$)-alkoxycarbonyl, carboxy, carbamoyl, mono-($C_1$–$C_4$) alkylcarbamoyl and di-($C_1$–$C_4$) alkylcarbamoyl groups; or 3) a group of the formula

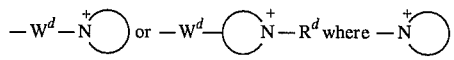

and $R^d$ are as defined above; $W^d$ is an oxygen atom or a straight or branched lower alkylene or alkenylene group which is uninterrupted or interrupted by an oxygen linkage;

or pharmaceutically acceptable salts or esters thereof.

3. A compound of claim 1 of the formula

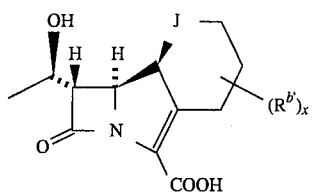

where x is 1; J is O or S; $R^b$ is a group of the formula $-(CH_2)_m-K^b-(CH_2)_n-U^{b'}$, where $K^b$ is $CH_2$, O, S or NH; m and n is each 0 to 3; $U^{b'}$ is (1) a basic group selected from the group consisting of an amino, alkylamino, amidino, alkylamidino and pyrrolidino groups, (2) a group of the formula

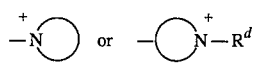

where said

is unsubstituted or substituted pyridinium, pyridazinzum, pyrimidinium, pyrazinium, pyrazolium, triazolium, imidazollum, thiazolium, oxazolium, thiadiazolium, isothiazolium, isoxazolium, N-methylpyrrolidinium, quinolinium, isoquinolinium, quinoxalinium, isocinnolinium, thienopyridinium, imidazolopyridinium, imidazolopyridazinium, triazolopyridinium, triazolopyridazinium, triazolopyridazinium, quinuclidinium or dihydropyrazolotriazolium; or (3) a group of the formula

where $R^d$ and $R^e$ each is an alkyl group, wherein said

or (2) above, $R^d$ and $R^e$ are unsubstituted or substituted with a substituent selected from the group consisting of ($C_1$–$C_6$) alkyl, ($C_2$–$C_6$) alkenyl, ($C_6$–$C_{10}$) aryl, ($C_7$–$C_{12}$) aralkyl, $C_3$–$C_6$) cycloalkyl, azetidine, furan, pyrrole, pyrrolidine, thiophene, tetrahydrothiophene, thiazole, isothiazole, thiazoline, thiazolidine, oxazole, isoxazole, oxazoline, oxazolidine, pyrazole, pyrazoline, imidazole, imidazoline, thiadiazole, triazole, tetrazole, pyridine, pyrimidine, pyridazine, triazine, morpholine, piperazine, piperidine, quinuclidine, cyano, amino, mono-($C_1$–$C_4$) alkylamino, di-($C_1$–$C_4$) alkylamino, acylamino, hydroxyl, ($C_1$–$C_4$) alkyloxy, acyloxy, carbamoyloxy, mono-($C_1$–$C_4$) alkylcarbamoyloxy, di-($C_1$–$C_4$) alkylcarbamoyloxy, ($C_1$–$C_4$) alkylthio, ($C_1$–$C_4$)-alkylsulfinyl, ($C_1$–$C_4$) alkylsulfonyl, ($C_1$–$C_4$) -alkylsulfonylamino, halogen, sulfamoyl, mono-($C_1$–$C_4$) alkylsulfamoyl, di-$C_1$–$C_4$) alkylsulfamoyl, ($C_1$–$C_4$) -alkoxycarbonyl, carboxy, carbamoyl, mono- ($C_1$–$C_4$) alkylcarbamoyl and di-($C_1$–$C_4$ ) alkylcarbamoyl groups; or pharmaceutically acceptable salts or esters thereof.

4. A compound of claim 2 of the formula

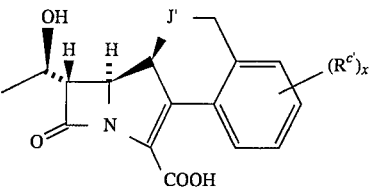

where x is 1, J' is O, S or $CH_2$; $R^c$ is (i) a group of the formula $-(CH_2)_m-K^c-(CH_2)_n-U^{c'}$ where $K^c$ is $CH_2$, S or NH; m and n each is a number from 0 to 3; $U^{c'}$ is (1) a basic group selected from the group consisting of an amino, alkylamino, amidino, alkylamidino and pyrrolidino basic groups, or (2) a group of the formula

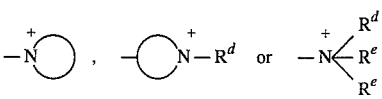

wherein

is unsubstituted or substituted pyridinium, pyridazinium, pyrimidinium, pyraginium, pyrazolium, triazolium, imidazolium, thiazolium, oxazolium, thiadiazolium, isothiazolium, isoxazolium, N-methylpyrrolidinium, quinolinium, isoquinolinium, quinoxalinium, isocinnolinium, thienopyridinium, imidazolopyridinium, imidazolopyridazinium, triazolopyridinium, triazolopyridazinium, triazolopyridazinium, quinuclidinium or dihydropyrazolotriazolium, $R^d$ and $R^e$ each is an alkyl group which is unsubstituted or substituted wherein said substituent is selected from the group consisting of ($C_1$–$C_6$) alkyl, ($C_2$–$C_6$) alkenyl, ($C_6$–$C_{10}$) aryl, ($C_7$–$C_{12}$) aralkyl, ($C_3$–$C_6$) cycloalkyl, azetidine, furan, pyrrole, pyrrolidine, thiophene, tetrahydrothiophene, thiazole,isothiazole, thiazoline, thiazolidine, oxazole, isoxazole, oxazoline, oxazolidine, pyrazole, pyrazoline, imidazole, imidazoline, thiadiazole, triazole, tetrazole, pyridine, pyrimidine, pyridazine, triazine, morpholine, piperazine, piperidine, quinuclidine, cyano, amino, mono-($C_1$–$C_4$) alkylamino, di-($C_1$–$C_4$) alkylamino, acylamino, hydroxyl, ($C_1$–$C_4$) alkyloxy, acyloxy, carbamoyloxy, mono-($C_1$–$C_4$) alkylcarbamoyloxy, di-($C_1$–$C_4$) alkylcarbamoyloxy, ($C_1$–$C_4$) alkylthio, ($C_1$–$C_4$)-alkylsulfinyl, ($C_1$–$C_4$) alkylsulfonyl, ($C_1$–$C_4$)-alkylsulfonylamino, halogen, sulfamoyl, mono-($C_1$–$C_4$) alkylsulfamoyl, di-($C_1$–$C_4$) alkylsulfamoyl, ($C_1$–$C_4$)-alkoxycarbonyl, carboxy, carbamoyl, mono-($C_1$–$C_4$) alkylcarbamoyl and di-($C_1$–$C_4$) alkylcarbamoyl groups; or (ii) a group of the formula $-(CH_2)_m-K^d-(CH_2)_n-U^d$ where $K^d$ is O; m and n each is a number from 0 to 3; $U^d$ is a group of the formula

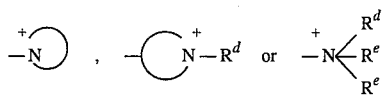

or a group of the formula

where

$R^d$ and $R^e$ are as defined above; or pharmaceutically acceptable salts or esters thereof.

5. A compound of claim 2 of the formula

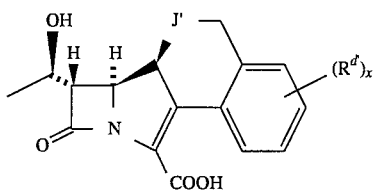

where x is 2, J' is O, S, or $CH_2$; $R^d$ are a pair of substituent groups, in the ortho position one from the other, one of which is a hydroxy group, the other being a hydroxy or alkylsulfonylamino group or pharmaceutically acceptable salts or esters thereof.

6. (5S,6R,7S,11R)- 5-[(R)-1-hydroxyethyl]-4-oxo-11-[2-(1-pyridinio)ethyl]- 3-azatricyclo[5.4.0.0$^{3,6}$]undec-1-ene-2-carboxylate.

7. (5S,6S,7S,11S)- 5-[(R)-1-hydroxyethyl]-4-oxo-11-[2-(1-pyridinio)ethyl]- 8-oxa-3-azatricyclo[5.4.0.0$^{3,6}$]undec-1-ene-2-carboxylate.

8. Sodium (5S, 6S, 7S, 11S)-5-[(R)-1-hydroxyethyl]-11-(2-hydroxyethyl)-4 -oxo-8-oxa-3-azatricyclo[5.4.0.0$^{3,6}$]undec-1-ene-2-carboxylate.

9. (5S, 6S, 7S, 11S)- 11-[(2-aminoethyl)thio]-5-[(R)-1-hydroxyethyl]-4-oxo-8 -oxa-3-azatricyclo[5.4.0.0$^{3,6}$]undec-1-ene-2-carboxylic acid.

10. An antibacterial composition which comprises an effective antibacterial amount of a compound as defined in claim 1, or its pharmaceutically acceptable salt or ester, and a pharmaceutically acceptable carrier, diluent or excipient.

11. An antibacterial composition which comprises an effective antibacterial amount of a compound as defined in claim 2, or its pharmaceutically acceptable salt or ester, and a pharmaceutically acceptable carrier, diluent or excipient.

* * * * *

UNITED STATES PATENT AND TRADEMARK OFFICE
CERTIFICATE OF CORRECTION

PATENT NO. : 5,459,260
DATED : Oct. 17, 1995
INVENTOR(S) : SENDAI et al.

It is certified that error appears in the above-indentified patent and that said Letters Patent is hereby corrected as shown below:

Column 2, lines 4 and 38, the formulas shown should appear as

Column 3, line 8, the formula shown should appear as

Column 5, lines 23 and 48, the formula shown should appear as

UNITED STATES PATENT AND TRADEMARK OFFICE
CERTIFICATE OF CORRECTION

PATENT NO. : 5,459,260
DATED : Oct. 17, 1995
INVENTOR(S) : SENDAI et al.

It is certified that error appears in the above-indentified patent and that said Letters Patent is hereby corrected as shown below:

Column 6, line 9, the formula shown should appear as

Column 49, claim 1, line 50, the formula shown should appear as

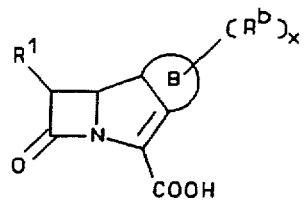

Signed and Sealed this

Twenty-seventh Day of February, 1996

Attest:

BRUCE LEHMAN

*Attesting Officer*  Commissioner of Patents and Trademarks